US011974973B2

(12) United States Patent
Kovacs et al.

(10) Patent No.: US 11,974,973 B2
(45) Date of Patent: May 7, 2024

(54) KETONE SUPPLEMENTS-EVOKED EFFECT ON ABSENCE EPILEPSY BY CO-ADMINISTRATION OF URIDINE

(71) Applicants: UNIVERSITY OF SOUTH FLORIDA, Tampa, FL (US); EÖTVÖS LORÁND UNIVERSITY, Budapest (HU)

(72) Inventors: Zsolt Kovacs, Tampa, FL (US); Csilla Ari D'Agostino, Tampa, FL (US); Dominic D'Agostino, Tampa, FL (US)

(73) Assignees: University of South Florida, Tampa, FL (US); Eötvös Loránd University, Budapest (HU)

( * ) Notice: Subject to any disclaimer, the term of this patent is extended or adjusted under 35 U.S.C. 154(b) by 0 days.

(21) Appl. No.: 17/576,375

(22) Filed: Jan. 14, 2022

(65) Prior Publication Data

US 2022/0218635 A1 Jul. 14, 2022

(51) Int. Cl.
| | |
|---|---|
| A61K 31/7072 | (2006.01) |
| A61K 31/19 | (2006.01) |
| A61K 31/225 | (2006.01) |
| A61K 31/23 | (2006.01) |
| A61K 31/519 | (2006.01) |
| A61K 31/522 | (2006.01) |
| A61K 45/06 | (2006.01) |
| A61P 25/14 | (2006.01) |

(52) U.S. Cl.
CPC ............ *A61K 31/19* (2013.01); *A61K 31/225* (2013.01); *A61K 31/23* (2013.01); *A61K 31/519* (2013.01); *A61K 31/522* (2013.01); *A61K 45/06* (2013.01); *A61P 25/14* (2018.01)

(58) Field of Classification Search
CPC ....... A61P 25/08; A61P 25/14; A61K 31/7072
See application file for complete search history.

(56) References Cited

U.S. PATENT DOCUMENTS 5,470,838 A 11/1995 von Borstel

FOREIGN PATENT DOCUMENTS

WO WO-2018081118 A1 * 5/2018 ............ A61K 31/19

OTHER PUBLICATIONS

Adenosine A1 Receptor Antagonism Abolished the Anti-seizure Effects of Exogenous Ketone Supplementation in Wistar Albino Glaxo Rijswijk Rats Kovács et.al. 10, Front. Mol. Neurosci. 235 (2017) (Year: 2017).*
A. Coenen et al., 33 Behavior Genetics, 635-655 (2003) (Year: 2003).*
Achanta, L.B.; Rae, C.D. β-Hydroxybutyrate in the brain: One molecule, multiple mechanisms. Neurochem. Res. 2017, 42, 35-49, doi:10.1007/s11064-016-2099-2.
Ari, C.; Kovács, Z.; Juhasz, G.; Murdun, C.; Goldhagen, C.R.; Koutnik, A.M.; Poff, A.M.; Kesl, S.L.; D' Agostino, D.P. Exogenous ketone supplements reduce anxiety-related behavior in Sprague-Dawley and Wistar Albino Glaxo/Rijswijk rats. Front. Mol. Neurosci. 2016, 9, 137, doi:10.3389/fnmol.2017.00036.
Ari, C.; Murdun, C.; Koutnik, A.P.; Goldhagen, C.R.; Rogers, C.; Park, C.; Bharwani, S.; Diamond, D.M.; Kindy, M.S.; D' Agostino, D.P.; et al. Exogenous ketones lower blood glucose level in rested and exercised rodent models. Nutrients 2019, 11, 2330, doi:10.3390/nu11102330.
Bourget, P.A.; Tremblay, G.C. Pyrimidine biosynthesis in rat brain. J. Neurochem. 1972, 19, 1617-1624, doi: 10.1111/j.1471-4159.1972.tb06207.x.
Ciarlone, S.L.; Grieco, J.C.; D' Agostino, D.P.; Weeber, E.J. Ketone ester supplementation attenuates seizure activity, and improves behavior and hippocampal synaptic plasticity in an Angelman syndrome mouse model. Neurobiol. Dis. 2016, 96, 38-46, doi:10.1016/j.nbd.2016.08.002.
Clarke, K.; Tchabanenko, K.; Pawlosky, R.; Carter, E.; Todd King, M.; Musa-Veloso, K.; Ho, M.; Roberts, A.; Robertson, J.; Vanitallie, T.B.; et al. Kinetics, safety and tolerability of (R)-3-hydroxybutyl (R)-3-hydroxybutyrate in healthy adult subjects. Regul. Toxicol. Pharmacol. 2012, 63, 401-408, doi:10.1016/j.yrtph.2012.04.008.
Coenen, A.M.; Van Luijtelaar, E.L. Genetic animal models for absence epilepsy: A review of the WAG/Rij strain of rats. Behav. Genet. 2003, 33, 635-655, doi:10.1023/A:1026179013847.
Cremer, C.M.; Palomero-Gallagher, N.; Bidmon, H.J.; Schleicher, A.; Speckmann, E.J.; Zilles, K. Pentylenetetrazole-induced seizures affect binding site densities for GABA, glutamate and adenosine receptors in the rat brain. Neuroscience 2009, 163, 490-499, doi: 10.1016/j.neuroscience.2009.03.068.
Cunha, R.A. Neuroprotection by adenosine in the brain: From A(1) receptor activation to A (2A) receptor blockade. Purinergic Signal. 2005, 1, 111-134, doi:10.1007/s11302-005-0649-1.
D' Agostino, D.; Pilla, R.; Held, H.; Landon, C.; Puchowicz, M.; Brunengraber, H.; Ari, C.; Arnold, P.; Dean, J.B. Therapeutic ketosis with ketone ester delays central nervous system oxygen toxicity seizures in rats. Am. J. Phys. Reg. Integr. Comp. Phys. 2013, 304, 829-836, doi:10.1152/ajpregu.00506.2012.
D' Alimonte, I., et al. Altered distribution and function of A2A adenosine receptors in the brain of WAG/Rij rats with genetic absence epilepsy, before and after appearance of the disease. Eur. J. Neurosci. 2009, 30, 1023-1035, doi:10.1111/j.1460-9568.2009.06897.x.
DeCampo, D.M.; Kossoff, E.H. Ketogenic dietary therapies for epilepsy and beyond. Curr. Opin. Clin. Nutr. Metab. Care. 2019, 22, 264-268, doi:10.1097/MCO.0000000000000565.
Depaulis, A.; Van Luijtelaar, G. Genetic models of absence epilepsy in the rat. In Models of Seizures and Epilepsy, 1st ed.; Pitkänen, A., Schwartzkroin, P.A., Moshé, S.L., Eds; Academic Press, San Diego, CA, USA, 2005; Chapter 18, pp. 233-248.
Dobolyi, A.; Juhász, G.; Kovács, Z.; Kardos, J. Uridine function in the central nervous system. Curr. Top. Med. Chem. 2011, 11, 1058-1067, doi:10.2174/156802611795347618.

(Continued)

*Primary Examiner* — Sikarl A Witherspoon
(74) *Attorney, Agent, or Firm* — Meunier Carlin & Curfman LLC

(57) ABSTRACT

Disclosed are methods of treating seizures in a subject. The methods can include administering to the subject in need thereof an effective amount of uridine source and a ketogenic composition including a ketogenic compound.

19 Claims, 6 Drawing Sheets

(56) References Cited

OTHER PUBLICATIONS

Freeman, J.M.; Vining, E.P.; Pillas, D.J.; Pyzik, P.L.; Casey, J.C.; Kelly, L.M. The efficacy of the ketogenic diet—1998: A prospective evaluation of intervention in 150 children. Pediatrics. 1998, 102, 1358-1363, doi:10.1542/peds.102.6.1358.
Haas, H.L.; Greene, R.W. Adenosine enhances afterhyperpolarization and accommodation in hippocampal pyramidal cells. Pflugers Arch. 1984, 402, 244-247, doi:10.1007/BF00585506.
Hashim, S.A .; VanItallie, T.B. Ketone body therapy: From the ketogenic diet to the oral administration of ketone ester. J. Lipid Res. 2014, 55, 1818-1826, doi: 10.1194/jlr.R046599.
Haskó, G.; Pacher, P.; Vizi, E.S.; Illes, P. Adenosine receptor signaling in the brain immune system. Trends Pharmacol. Sci. 2005, 26, 511-516, doi:10.1016/j.tips.2005.08.004.
Ipata, P.L.; Camici, M.; Micheli, V.; Tozz, M.G. Metabolic network of nucleosides in the brain. Curr. Top. Med. Chem. 2011, 11, 909-922, doi:10.2174/156802611795347555.
Johannes Koch, et al., "CAD mutations and uridine-responsive epileptic Encephalopathy", Brain 2017: 140:2; 279-286.
Juge, N.; Gray, J.A.; Omote, H.; Miyaji, T.; Inoue, T.; Hara, C.; Uneyama, H.; Edwards, R.H.; Nicoll, R.A.; Moriyama, Y. Metabolic control of vesicular glutamate transport and release. Neuron 2010, 68, 99-112, doi:10.1016/j.neuron.2010.09.002.
Kardos, J.; Kovács, I.; Szárics, E.; Kovács, R.; Skuban, N.; Nyitrai, G.; Dobolyi, A.; Juhász, G. Uridine activates fast transmembrane Ca2+ ion fluxes in rat brain homogenates. Neuroreport 1999, 10, 1577-1582, doi:10.1097/00001756-199905140-00034.
Kimura, T.; Ho, I.K.; Yamamoto, I. Uridine receptor: Discovery and its involvement in sleep mechanism. Sleep 2001, 24, 251-260, doi:10.1093/sleep/24.3.251.
Kimura, T.; Miki, M.; Ikeda, M.; Yonemoto, S.; Watanabe, K.; Kondo, S.; Ho, I.K.; Yamamoto, I. Possible existence of a novel receptor for uridine analogues in the central nervous system using two isomers, N3-(S)-(+)- and N3-(R)-(−)-alpha- hydroxy-beta-phenethyluridines. Biol. Pharm. Bull. 2001, 24, 729-731, doi:10.1248/bpb.24.729.
Koch, J.; Mayr, J.A.; Alhaddad, B.; Rauscher, C.; Bierau, J .; Kovacs-Nagy, R.; Coene, K.L.; Bader, I.; Holzhacker, M.; Prokisch, H.; et al. CAD mutations and uridine-responsive epileptic encephalopathy. Brain 2017, 140, 279-286, doi:10.1093/brain/aww300.
Kovács, Z., et al., "Area, age and gender dependence of the nucleoside system in the brain: A review of current literature", Curr. Top. Med. Chem., 2011, 11, 1012-1033, doi:10.2174/156802611795347636.
Kovács, Z., et al., Adenosine A1 Receptor Antagonism Abolished the Anti-seizure Effects of Exogenous Ketone Supplementation in Wistar Albino Glaxo Rijswijk Rats. Front. Mol. Neurosci. vol. 10, 2017, p. 235.
Kovács, Z., et al., Exogenous Ketone Supplementation Decreased the Lipopolysaccharide-Induced Increase in Absence Epileptic Activity in Wistar Albino Glaxo Rijswijk Rats. Front. Mol. Neurosci. 2019, 12, 45.
Kovács, Z.; Czurkó, A.; Kékesi, K.A.; Juhász, G. The effect of intraperitoneally administered dimethyl sulfoxide on absence-like epileptic activity of freely moving WAG/RIJ rats. J. Neurosci. Methods 2011, 197, 133-136, doi:10.1016/j.jneumeth.2011.02.005.
Kovács, Z.; D' Agostino, D.P.; Diamond, D.; Kindy, M.S.; Rogers, C.; Ari, C. Therapeutic Potential of Exogenous Ketone Supplement Induced Ketosis in the Treatment of Psychiatric Disorders: Review of Current Literature. Front. Psychiatry 2019, 10, 363, doi:10.3389/fpsyt.2019.00363.
Kovács, Z.; Dobolyi, Á.; Kékesi, A.; Juhász, G. 5'-nucleotidases, nucleosides and their distribution in the brain: Pathological and therapeutic implications. Curr. Med. Chem. 2013, 20, 4217-4240, doi:10.2174/0929867311320340003.
Kovács, Z.; Kékesi, K.A.; Dobolyi, Á.; Lakatos, R.; Juhász, G. Absence epileptic activity changing effects of non-adenosine nucleoside inosine, guanosine and uridine in Wistar Albino Glaxo Rijswijk rats. Neuroscience 2015, 300, 593-608, doi:10.1016/j.neuroscience.2015.05.054.
Kovács, Z.; Kékesi, K.A.; Juhász, G.; Dobolyi, A. The antiepileptic potential of nucleosides. Curr. Med. Chem. 2014, 21, 788-821, doi:10.2174/1381612819666131119154505.
Kovács, Z.; Kékesi, K.A.; Szilágyi, N.; Ábrahám, I.; Székács, D.; Király, N.; Papp, E.; Császár, I.; Szego, E.; Barabás, K.; et al. Facilitation of spike-wave discharge activity by lipopolysaccharides in Wistar Albino Glaxo/Rijswijk rats. Neuroscience 2006, 140, 731-742, doi:10.1016/j.neuroscience.2006.02.023.
Kovács, Z.; Slézia, A.; Bali, Z.K.; Kovács, P.; Dobolyi, A.; Szikra, T.; Hernádi, I.; Juhász, G. Uridine modulates neuronal activity and inhibits spike-wave discharges of absence epileptic Long Evans and Wistar Albino Glaxo/Rijswijk rats. Brain Res. Bull. 2013, 97, 16-23, doi:10.1016/j.brainresbull.2013.05.009.
Lakatos, R.K.; Dobolyi, Á.; Todorov, M.I.; Kékesi, K.A.; Juhász, G.; Aleksza, M.; Kovács, Z. Guanosine may increase absence epileptic activity by means of A2A adenosine receptors in Wistar Albino Glaxo Rijswijk rats. Brain Res. Bull. 2016, 124, 172-181, doi:10.1016/j.brainresbull.2016.05.001.
Liu, P.; Che, X.; Yu, L.; Yang, X.; An, N.; Song, W.; Wu, C.; Yang, J. Uridine attenuates morphine-induced conditioned place preference and regulates glutamate/GABA levels in mPFC of mice. Pharmacol. Biochem. Behav. 2017, 163, 74-82, doi:10.1016/j.pbb.2017.10.004.
Lund, T.M.; Ploug, K.B.; Iversen, A.; Jensen, A.A.; Jansen-Olesen, I. The metabolic impact of β-hydroxybutyrate on neurotransmission: Reduced glycolysis mediates changes in calcium responses and KATP channel receptor sensitivity. J. Neurochem. 2015, 132, 520-531, doi:10.1111/jnc.12975.
Lusardi, T.A.; Akula, K.K.; Coffman, S.Q.; Ruskin, D.N.; Masino, S.A.; Boison, D. Ketogenic diet prevents epileptogenesis and disease progression in adult mice and rats. Neuropharmacology 2015, 99, 500-509, doi:10.1016/j.neuropharm.2015.08.007.
Martin-McGill, K.J.; Bresnahan, R.; Levy, R.G.; Cooper, P.N. Ketogenic diets for drug-resistant epilepsy. Cochrane Database Syst. Rev. 2020, 6, CD001903, doi:10.1002/14651858.CD001903.pub5.
Masino, S.A.; Kawamura, M.; Wasser, C.D.; Pomeroy, L.T.; Ruskin, D.N. Adenosine, ketogenic diet and epilepsy: The emerging therapeutic relationship between metabolism and brain activity. Curr. Neuropharmacol. 2009, 7, 257-268, doi:10.2174/157015909789152164.
Masino, S.A.; Li, T.; Theofilas, P.; Sandau, U.S.; Ruskin, D.N.; Fredholm, B.B.; Geiger, J.D.; Aronica, E.; Boison, D. A ketogenic diet suppresses seizures in mice through adenosine A1 receptors. J. Clin. Investig. 2011, 121, 2679-2683, doi:10.1172/JCI57813.
McNally, M.A.; Hartman, A.L. Ketone bodies in epilepsy. J. Neurochem. 2012, 121, 28-35, doi:10.1111/j.1471-4159.2012.07670.x.
Meeren, H.K.; Pijn, J.P.; Van Luijtelaar, E.L.; Coenen, A.M.; Lopes da Silva, F.H. Cortical focus drives widespread corticothalamic networks during spontaneous absence seizures in rats. J. Neurosci. 2002, 22, 1480-1495, doi:10.1523/JNEUROSCI.22-04-01480.2002.
Newman, J.C.; Verdin, E. Ketone bodies as signaling metabolites. Trends Endocrinol. Metab. 2014, 25, 42-52, doi:10.1016/j.tem.2013.09.002.
Poff, A.M.; Rho, J.M.; D' Agostino, D.P. Ketone administration for seizure disorders: History and rationale for ketone esters and metabolic alternatives. Front. Neurosci. 2019, 13, 1041, doi:10.3389/fnins.2019.01041.
Pooler, A.M.; Guez, D.H.; Benedictus, R.; Wurtman, R.J. Uridine enhances neurite outgrowth in nerve growth factor-differentiated pheochromocytoma cells. Neuroscience 2005, 134, 207-214, doi:10.1016/j.neuroscience.2005.03.050.
Roberts, C.A. Anticonvulsant effects of uridine: Comparative analysis of metrazol and penicillin induced foci. Brain Res. 1973, 55, 291-308, doi:10.1016/0006-8993(73)90296-5.
Rogawski, M.A.; Löscher, W.; Rho, J.M. Mechanisms of Action of Antiseizure Drugs and the Ketogenic Diet. Cold Spring Harb. Perspect. Med. 2016, 6, a022780, doi:10.1101/cshperspect.a022780.

(56) References Cited

OTHER PUBLICATIONS

Ruskin, D.N.; Kawamura, M.; Masino, S.A. Adenosine and Ketogenic Treatments. J. Caffeine Adenosine Res. 2020, 10, 104-109, doi:10.1089/caff.2020.0011.

Sada, N.; Inoue, T. Electrical control in neurons by the ketogenic diet. Front. Cell Neurosci. 2018, 12, 208, doi:10.3389/fncel.2018.00208.

Sakamoto, T.; Cansev, M.; Wurtman, R.J. Oral supplementation with docosahexaenoic acid and uridine-5'-monophosphate increases dendritic spine density in adult gerbil hippocampus. Brain Res. 2007, 1182, 50-59, doi:10.1016/j.brainres.2007.08.089.

Schäfers, M.; Sorkin, L. Effect of cytokines on neuronal excitability. Neurosci. Lett. 2008, 437, 188-193, doi:10.1016/j.neulet.2008.03.052.

Sharma, A.K.; Rani, E.; Waheed, A.; Rajput, S.K. Pharmacoresistant epilepsy: A current update on non-conventional pharmacological and non-pharmacological interventions. J. Epilepsy Res. 2015, 5, 1-8, doi:10.14581/jer.15001.

Simeone, T.A.; Simeone, K.A.; Rho, J.M. Ketone bodies as anti-seizure agents. Neurochem. Res. 2017, 42, 2011-2018, doi:10.1007/s11064-017-2253-5.

Simeone, T.A.; Simeone, K.A.; Stafstrom, C.E.; Rho, J.M. Do ketone bodies mediate the anti-seizure effects of the ketogenic diet? Neuropharmacology 2018, 133, 233-241, doi:10.1016/j.neuropharm.2018.01.011.

Sitnikova, E.; van Luijtelaar, G. Electroencephalographic precursors of spike-wave discharges in a genetic rat model of absence epilepsy: Power spectrum and coherence EEG analyses. Epilepsy Res. 2009, 84, 159-171, doi:10.1016/j.eplepsyres.2009.01.016.

Sperlágh, B.; Szabó, G.; Erdélyi, F.; Baranyi, M.; Vizi, E.S. Homo- and heteroexchange of adenine nucleotides and nucleosides in rat hippocampal slices by the nucleoside transport system. Br. J. Pharmacol. 2003, 139, 623-633, doi:10.1038/sj.bjp.0705285.

Tianlin Wang, et al., "Antiepileptic effect of uridine may be caused by regulating dopamine release and receptor expression in corpus striatum", Brain Research, 1688 (2018) 47-53.

Ułamek-Kozioł, M.; Czuczwar, S.J.; Januszewski, S.; Pluta, R. Ketogenic diet and epilepsy. Nutrients 2019, 11, 2510, doi:10.3390/nu11102510.

Veech, R.L. The therapeutic implications of ketone bodies: The effects of ketone bodies in pathological conditions: Ketosis, ketogenic diet, redox states, insulin resistance, and mitochondrial metabolism. Prostaglandins Leukot. Essent. Fatty Acids 2004, 70, 309-319, doi:10.1016/j.plefa.2003.09.007.

Vining, E.P.; Freeman, J.M.; Ballaban-Gil, K.; Camfield, C.S.; Camfield, P.R.; Holmes, G.L.; Shinnar, S.; Shuman, R.; Trevathan, E.; Wheless, J.W. A multicenter study of the efficacy of the ketogenic diet. Arch. Neurol. 1998, 55, 1433-1437, doi:10.1001/archneur.55.11.1433.

Ye, F.; Li, X.J.; Jiang, W.L.; Sun, H.B.; Liu, J. Efficacy of and patient compliance with a ketogenic diet in adults with intractable epilepsy: A meta-analysis. J. Clin. Neurol. 2015, 11, 26-31, doi:10.3988/jcn.2015.11.1.26.

Yudkoff, M.; Daikhin, Y.; Melø, T.M.; Nissim, I.; Sonnewald, U.; Nissim, I. The ketogenic diet and brain metabolism of amino acids: Relationship to the anticonvulsant effect. Annu. Rev. Nutr. 2007, 27, 415-430, doi:10.1146/annurev.nutr.27.061406.093722.

Zhang, Y.; Guo, S.; Xie, C.; Fang, J. Uridine metabolism and its role in glucose, lipid, and amino acid homeostasis. Biomed. Res. Int. 2020, 2020:7091718, doi:10.1155/2020/7091718.

Zhao, Q.; Marolewski, A.; Rusche, J.R.; Holmes, G.L. Effects of uridine in models of epileptogenesis and seizures. Epilepsy Res. 2006, 70, 73-82, doi:10.1016/j.eplepsyres.2006.03.003.

Zhao, Q.; Shatskikh, T.; Marolewski, A.; Rusche, J.R.; Holmes, G.L. Effects of uridine on kindling. Epilepsy Behav. 2008, 13, 47-51, doi:10.1016/j.yebeh.2008.02.002.

* cited by examiner

KETONE SUPPLEMENTS-EVOKED EFFECT ON ABSENCE EPILEPSY BY CO-ADMINISTRATION OF URIDINE

CROSS-REFERENCE TO RELATED APPLICATIONS

This application claims the benefit of priority to U.S. Provisional Application No. 63/199,647, filed Jan. 14, 2021, which is incorporated by reference herein in its entirety.

BACKGROUND

A seizure is a change in sensation, awareness, or behavior brought about by a brief electrical disturbance in the brain. Seizures vary from a momentary disruption of the senses to short periods of unconsciousness or staring spells, to convulsions. Some people have just one type of seizure. Others have more than one type. All seizures are caused by the same thing: a sudden change in how the cells of the brain send electrical signals to each other.

During epilepsy, a propagation of high frequency, continuous firing is initiated, referred to as a seizure. The severity and symptoms of this seizure will depend on the position of the initial focal point, seizure length, frequency of the discharges and the distance the propagation spreads. Essentially, what a patient experiences during a seizure will depend on where in the brain the epileptic activity begins and how widely and rapidly it spreads. Neurons may fire up to 500 times a second during an epileptic seizure, over six times the normal rate of about 80 times a second. The onset of epilepsy is defined as a condition characterized by recurrent, unprovoked seizures.

There are over 40 different types of seizures, ranging from seizures that go totally unnoticed by others to tonic-clonic seizures which involve muscular contraction, uncontrollable jerks and loss of consciousness. Knowing which type of seizures a person has is useful as this will determine which antiepileptic drug (AED) is most likely to be of benefit. However, the choice of the AED also depends on several other issues, including the age and sex of the patient, requirements for compliance and the presence of hard-to-treat epileptic syndromes.

There is a need for compositions and methods to effectively treat or prevent seizures in a subject.

The compositions and methods disclosed herein address these and other needs.

SUMMARY

Disclosed herein a method of treating seizures in a subject. The method can include administering to the subject in need thereof an effective amount of uridine source and a ketogenic composition including a ketogenic compound.

In some embodiments, the ketogenic compound can include a ketone ester, a ketone salt, a ketone body precursor, or a combination thereof. In some embodiments, the ketogenic compound can include a ketone salt. In some embodiments, the ketone salt can be a β-hydroxybutyrate salt. In some embodiments, the ketone salt can be a β-hydroxybutyrate mineral salt. In some embodiments, the β-hydroxybutyrate mineral salt can be a $Na^+Ca^{2+}$ β-hydroxybutyrate mineral salt.

In some embodiments, the ketogenic compound can include a ketone ester. In some embodiments, the ketone ester can be 1,3-butanediol-acetoacetate diester. In some embodiments, the ketogenic composition can further include a medium chain triglyceride. In some embodiments, the ketogenic composition can include a ketone salt and a medium chain triglyceride. In some embodiments, the ketone salt and the medium chain triglyceride can have an approximate 1:1 ratio. In some embodiments, the method can further include administering an anti-epileptic agent, an anti-convulsant agent, or a combination thereof. In some embodiments, the method can prevent seizures in the subject. In some embodiments, the method can delay the onset of seizures in the in the subject. In some embodiments, the method can reduce the severity of seizures in the subject. In some embodiments, the subject can be diagnosed with a seizure disorder. In some embodiments, the seizure disorder can be epilepsy. In some embodiments, the composition can be administered orally, intraperitoneally, or a combination thereof. In some embodiments, the method can suppress spike wave discharges in a subject.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

(FIG. 2A); i.p. 1000 mg/kg; (FIG. 2B)) alone, DPCPX (i.p. 0.2 mg/kg) (FIG. 2C) and SCH 58261 (i.p. 0.5 mg/kg) (FIG. 2D) alone as well as combined administration of DPCPX (i.p. 0.2 mg/kg) with uridine (i.p. 1000 mg/kg) (FIG. 2E) and SCH 58261 (i.p. 0.5 mg/kg) with uridine (i.p. 1000 mg/kg) (FIG. 2F) on SWD number. Influence of combined administration of DPCPX (i.p. 0.2 mg/kg) with uridine (i.p. 1000 mg/kg) and SCH 58261 (i.p. 0.5 mg/kg) with uridine (i.p. 1000 mg/kg) on averaged SWD time (FIG. 2G) and total SWD time (FIG. 2H) between 150 and 210 min. Abbreviations: Co, control; DPCPX, 1,3-dipropyl-8-cyclopentylxanthine; D+Urd: DPCPX+URD; i.p., intraperitoneal; PTC or PTC day, post-treatment control day; SCH 58261, (7-(2-phenylethyl)-5-amino-2-(2-furyl)-pyrazolo-[4,3-e]-1,2,4-triazolo[1,5-c]pyrimidine); S+Urd: SCH 58261+URD; SWD, spike-wave discharge; URD, uridine. *: $p<0.05$, : $p<0.01$, *: $p<0.001$, ****: $p<0.0001$.

Like reference symbols in the various drawings indicate like elements.

DETAILED DESCRIPTION

Figure 1:
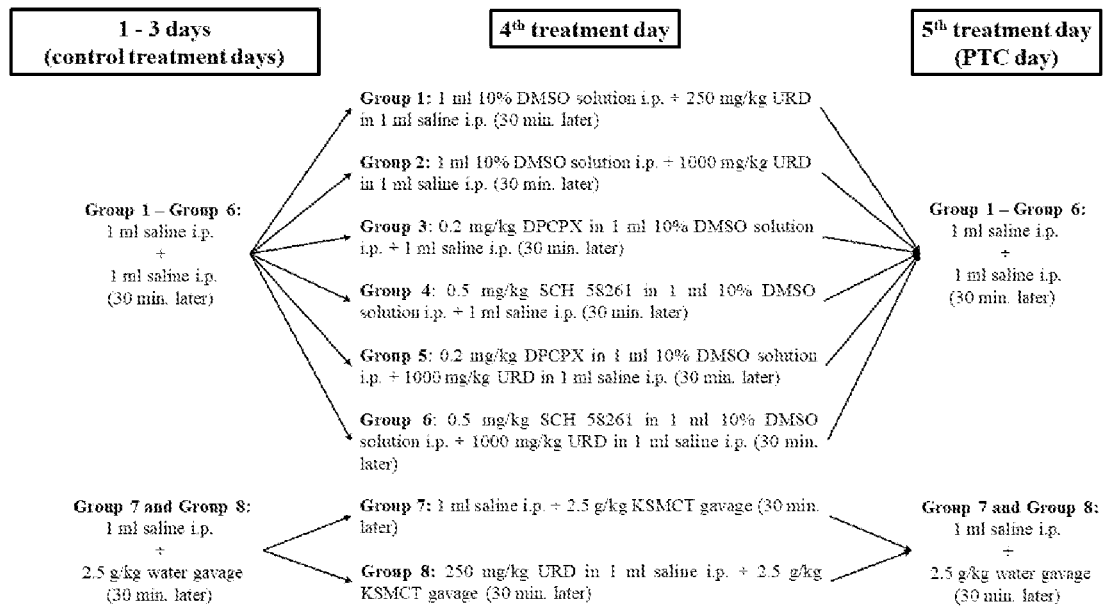
FIG. 1 shows details of the experimental protocol of the 8 treatment groups. Abbreviations: DMSO, dimethyl sulfoxide; DPCPX, 1,3-dipropyl-8-cyclopentylxanthine; Group: animal group; i.p., intraperitoneal; KSMCT, mix of ketone salt (KS) and medium chain triglyceride (MCT) oil in a 1:1 ratio; PTC day, post-treatment control day; SCH 58261, (7-(2-phenylethyl)-5-amino-2-(2-furyl)-pyrazolo-[4,3-e]-1,2,4-triazolo[1,5-c]pyrimidine); URD, uridine.

A number of embodiments of the disclosure have been described. Nevertheless, it will be understood that various modifications may be made without departing from the spirit and scope of the invention. Accordingly, other embodiments are within the scope of the following claims.

To facilitate understanding of the disclosure set forth herein, a number of terms are defined below. Unless defined otherwise, all technical and scientific terms used herein generally have the same meaning as commonly understood by one of ordinary skill in the art to which this disclosure belongs. Publications cited herein and the materials for which they are cited are specifically incorporated by reference.

General Definitions

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. Other than where noted, all numbers expressing quantities of ingredients, reaction conditions, geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Accordingly, these terms are intended to not only cover the recited element(s) or step(s), but may also include other elements or steps not expressly recited. Furthermore, as used herein, the use of the terms "a", "an", and "the" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. A range may be construed to include the start and the end of the range. For example, a range of 10% to 20% (i.e., range of 10%-20%) can includes 10% and also includes 20%, and includes percentages in between 10% and 20%, unless explicitly stated otherwise herein.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Administration" to a subject includes any route of introducing or delivering to a subject an agent. Administration can be carried out by any suitable route, including oral, topical, transcutaneous, transdermal, intra-joint, intra-arteriole, intradermal, intraventricular, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

A "decrease" can refer to any change that results in a smaller amount of a symptom, disease, composition, condition, or activity. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Inactivate", "inactivating" and "inactivation" means to decrease or eliminate an activity, response, condition, disease, or other biological parameter due to a chemical (covalent bond formation) between the ligand and a its biological target.

By "reduce" or other forms of the word, such as "reducing" or "reduction," is meant lowering of an event or characteristic (e.g., seizure). It is understood that this is typically in relation to some standard or expected value, in other words it is relative, but that it is not always necessary for the standard or relative value to be referred to.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms. As used herein, the term "preventing" a disorder or unwanted physiological event in a subject refers specifically to the prevention of the occurrence of symptoms and/or their underlying cause, wherein the subject may or may not exhibit heightened susceptibility to the disorder or event. In particular embodiments, "prevention" includes reduction in risk of coronavirus infection in patients. However, it will be appreciated that such prevention may not be absolute, i.e., it may not prevent all such patients developing a coronavirus infection, or may only partially prevent an infection in a single individual. As such, the terms "prevention" and "prophylaxis" may be used interchangeably.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts. An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

A "control" is an alternative subject or sample used in an experiment for comparison purposes. A control can be "positive" or "negative."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician. Administration of the therapeutic agents can be carried out at dosages and for periods of time effective for treatment of a subject. In some embodiments, the subject is a human.

"Esterification" refers to the reaction of an alcohol with a carboxylic acid or a carboxylic acid derivative to give an ester.

"Transesterification" refers to the reaction of an ester with an alcohol to form a new ester compound.

The terms "beta-hydroxybutyrate," "βHB", or "BHB" as used interchangeably herein refer to a carboxylic acid having the general formula $CH_3CHOHCH_2COOH$. βHB is a ketone body which may be utilized by the body as a fuel source during instances of low glucose levels.

The term "ketogenic composition" as used herein refers to a composition comprising one or more ketogenic compounds.

"Ketogenic compound" refers a compound that is capable of elevating ketone body concentrations in a subject. The ketone compound can be derived from, for example, a ketone body precursor, a ketone ester, a ketone salt, or a combination thereof.

"Ketone" or "ketone body", as used interchangeably herein, refers to a compound or species which is β-hydroxybutyrate (βHB), acetoacetate, acetone, or a combination thereof. A ketone body may be derived from a ketone body precursor, that is, a compound or species which is a precursor to a ketone body and which may be converted or metabolized to a ketone body in a subject.

"Ketone body ester" or "ketone ester" as used herein, refer to an ester of a ketone body, ketone body precursor, or derivative thereof. Any suitable ketone ester known in the art may be used. For example, the ketone ester may be 1,3 butanediol acetoacetate di ester.

"Ketone body salt" or "ketone salt" is a salt of a ketone body, ketone body precursor, or derivative thereof. The ketone salt may be combined with one or more monovalent cations, divalent cations, or alkaline amino acids. Any suitable ketone salt known in the art may be used.

The terms "ketogenic state" or "ketosis" as used interchangeably herein, refer to a subject having blood ketone body levels within the range of about 0.5 mmol/L to about 10 mmol/L. Levels above 10 mmol/L associated with ketoacidosis. Ketosis may be achieved in a subject by administering a ketogenic diet or a composition including a ketogenic compound.

"Ketogenic diet" as used herein refers to a diet that causes a metabolic switch from burning glucose for energy to burning fats for energy. Nutritional ketosis/ketogenic state may be achieved through calorie restriction, fasting, prolonged exercise, and/or a ketogenic diet that is high in fat and restricted in carbohydrates (e.g. sugars).

"Non-ketogenic diet" as used herein refers to a diet that is not capable of achieving ketosis or a ketogenic state in a subject.

The term "medium chain triglycerides" (MCT) as used herein refers to molecules having a glycerol backbone attached to three medium chain fatty acids. Medium chain fatty acids range from 6 to 12 carbon atoms in length. Exemplary fatty acids are caprylic acid, also known as octanoic acid, comprising 8 carbon molecules, and capric acid, also known as decanoic acid, comprising 10 carbon molecules.

Reference will now be made in detail to specific aspects of the disclosed materials, compounds, compositions, articles, and methods, examples of which are illustrated in the accompanying Examples and Figures.

Methods of Use

Disclosed herein are methods of treating seizures in a subject. The methods can include administering to the subject in need thereof an effective amount of uridine source and a ketogenic composition. In some embodiments, the administration of uridine source in combination with a ketogenic composition can prevent seizures in the subject. In some embodiments, the administration of uridine source in combination with a ketogenic composition can delay the onset of seizures in the subject. In some embodiments, the administration of uridine source in combination with a ketogenic composition can reduce the severity of seizures in the subject. In some embodiments, the administration of uridine source in combination with a ketogenic composition can suppress spike wave discharges in the subject.

In some embodiments, the subject may be diagnosed with a seizure disorder. The seizure disorder can be any condition in which seizures may be a symptom. In some embodiments, for example, the subject can be diagnosed with epilepsy. In some embodiments, the subject can be diagnosed with absence epilepsy, drug-resistant epilepsy, or (super-refractory) status epilepticus and febrile infection-related epilepsy syndrome.

In some embodiments, the subject is on a non-ketogenic diet. In some embodiments, the subject is on a standard diet. In some embodiments, the subject is on a non-ketogenic diet. In an embodiment, a ketogenic diet may comprise foods that are high in fat, low in carbohydrates, and provide adequate protein. The ketogenic diet can include from 60.0% to 90.0% fat. For example, the ketogenic diet can include 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90%. In another embodiment, the ketogenic diet can include from 10.0% to 25.0% protein. For example, the ketogenic diet can include 10%, 11%, 12%, 13%, 14%, 15%, 16%, 17%, 18%, 19%, 20%, 21%, 22%, 23%, 24%, or 25%. In yet another embodiment, the ketogenic diet can include from 0.1% to 5.0% carbohydrate. For example, the ketogenic diet can include 0.1%, 0.2%, 0.3%, 0.4%, 0.5%, 0.6%, 0.7%, 0.8%, 0.9%, 1.0%, 2.0%, 3.0%, 4.0%, or 5.0%. In a preferred embodiment, the ketogenic diet can include of 77.1% fat, 22.4% protein, and 0.5% carbohydrate.

Preferably, the ketogenic diet includes a caloric density from 4 Kcal/g to 8 Kcal/g. For example, the ketogenic diet can be 4 Kcal/g, 5 Kcal/g, 6 Kcal/g, 7 Kcal/g, or 8 Kcal/g. In a preferred embodiment, the caloric density can be 4 Kcal/g, such as 4.1 Kcal/g, 4.2 Kcal/g, 4.3 Kcal/g, 4.4 Kcal/g, 4.5 Kcal/g, 4.6 Kcal/g, 4.7 Kcal/g, 4.8 Kcal/g, 4.9 Kcal/g, 5.0 Kcal/g. In a preferred embodiment, the ketogenic diet can include a caloric density of 4.7 Kcal/g.

The levels of circulating glucose and ketone bodies may be measured in a subject prior to or following administration of uridine source in combination with a ketogenic composition. Circulating levels may be determined from, for example, bodily fluids (e.g. blood, serum, plasma, or urine) or breath (such as, acetone on the breath). Any suitable measuring device or kit known in the art may be used, such as the PRECISION XTRA® blood glucose and ketone monitoring kit (Abbott Laboratories, Abbott Park, IL).

Uridine source in combination with a ketogenic composition can be administered in various ways, including, for example, orally, intragastrically, or parenterally (referring to intravenously and intra-arterially and other appropriate parenteral routes), among others. Administration can be as a single dose, or multiple doses over a period of time. Administration can be as a single dose, or multiple doses over a period of time. In an embodiment, uridine source in combination with a ketogenic composition can be administered chronically, for example, between about 1 day and about 7 days), or sub-chronically (e.g., more than 7 days). For example, multiple doses can be delivered over 1 day, 3 days, 5 days, 7 days, 10 days, 14 days, or more, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or more, 1 month, 2 months, 3 months, 4 months, 5 months, 6 months, 7 months, 8 months, 9 months, 10 months, 11 months, 12 months, or more.

Uridine source and the ketogenic composition can be administered simultaneously or sequentially. Sequential administration can include administration of uridine source before or after administration of the ketogenic composition. In other embodiments, there can be an interval of time between administration of uridine source and the administration of a ketogenic composition. In some embodiments, uridine source can be administered simultaneously with the administration of a ketogenic composition. In some embodiments, uridine source and the ketogenic composition can be administered in the same formulation. In some embodiments, administration of uridine source in combination with a ketogenic composition can allow lower doses and/or administration at less frequent intervals than when each is used individually.

Ketogenic Compositions

In the methods described herein, uridine source in combination with ketogenic composition can be administered. In some embodiments, the ketogenic compound can be any compound capable of elevating ketone body concentrations in a subject. For example, the ketogenic compound can elevate expression of βHB following administration to the subject. The ketogenic compound can be a ketone body precursor, a ketone ester, a ketone salt, or a combination thereof. For example, the ketogenic compound can be a ketone body precursor or derivative thereof. Any suitable ketone body precursor which can be metabolized into a ketone body upon administration to the subject can be used. For example, the ketogenic compound can be 1,3-butanediol, acetoacetate, or βHB moieties or derivatives thereof, including esters and salts thereof. For example, the ketogenic compound can be 1,3-butanediol-acetoacetate diester. The ketogenic compound may be sodium-3-hydroxybutyrate. The ketogenic compound may be R,S-sodium-3-hydroxybutyrate.

In some embodiments, the ketogenic compound can include a ketone ester. Suitable ketone ester can be prepared using any suitable physiologically compatible alcohol. Examples of polyhydric alcohols suitable for preparing such esters include carbohydrates and carbohydrate derivatives, such as carbohydrate alcohols. Examples of carbohydrates include, without limitation, altrose, arabinose, dextrose, erythrose, fructose, galactose, glucose, gulose, idose, lactose, lyxose, mannose, ribose, sucrose, talose, threose, xylose and the like. In some embodiments, the ketone ester can be a monoester, a diester, a polyester, or any combination thereof. In some embodiments, the ketone ester can be a diester. In some embodiments, the ketone ester can be a polyester. In some embodiments, the ketone ester can be a glycerol monoester or diester. In an embodiment, the monoester may be esterified at the 1 position. In another embodiment, the diester may be esterified at the 1 and 3 positions. In an embodiment, the ketone ester may comprise a monoester of butane-1,3-diol with D-3-hydroxybutyrate or L-3-hydroxybutyrate, for example 3-hydroxybutyl-L,D-P-hydroxybutyrate, and a monoester and a diester of glycerol with D-3-hydroxybutyrate or L-3-hydroxybutyrate. The ester may be in an enantiomerically enriched form. In some embodiments, the ketone ester can be a monoester. In some embodiments, for example, the ketone ester can be 1,3-butanediol-acetoacetate monoester, 1,3-butanediol-acetoacetate diester, or a combination thereof.

In some embodiments, the ketogenic compound can be a ketone salt. The ketone salt can be combined with a monovalent cation, divalent cation, or alkaline amino acid. Any suitable ketone salt can be used. For example, the ketone salt can be a βHB salt. The ketone salt can be a βHB mineral salt. For example, the βHB mineral salt can be potassium βHB, sodium βHB, calcium βHB, magnesium βHB, lithium BHB, or any other feasible non-toxic mineral salts of βHB. The ketone salt can be a βHB organic salt. Organic salts of βHB include salts of organic bases such as arginine lysine histidine ornithine creatine agmatine βHB, or citrulline βHB. The ketone salt can be a combination of βHB salts. For example, the ketone salt can be a sodium/potassium βHB mineral salt ($Na^+K^+\beta HB$). The ketone salt can be a sodium/calcium βHB mineral salt ($Na^+Ca^{2+}$ βHB).

The ketone salt can be mixed into a solution. For example, a βHB mineral salt can be mixed into a solution. The βHB mineral salt can be from 1 to 99% of a solution. For example, the βHB mineral salt can be 5-95%, 10-90%, 20-80%, 30-70%, 40-60%, or about 50% of a solution.

In some embodiments, the ketogenic composition can further include a medium chain fatty acid or ester thereof. In some embodiments, the composition can include MCT oil. Sources of the medium chain fatty acid or an ester thereof include coconut oil, coconut milk powder, fractionated coconut oil, palm oil, palm kernel oil, caprylic acid, isolated medium chain fatty acids such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, or salts of the medium chain triglycerides. Ester derivatives can optionally include alkyl ester derivatives, such as methyl, ethyl, propyl, butyl, hexyl, etc. Derivatives can be prepared by any process known in the art, such as direct esterification, rearrangement, fractionation, transesterification, or the like.

In some embodiments, the ketogenic composition can include a ketone ester, a ketone salt, a ketone body precursor, and a medium chain fatty acid. In some embodiments, the ketogenic composition can include a ketone ester, a ketone salt, and a ketone body precursor. In some embodiments, the ketogenic composition can include a ketone ester and a ketone salt. In some embodiments, the ketogenic composition can include a ketone salt, a ketone ester, and a medium chain fatty acid. In some embodiments, the ketogenic composition can include a ketone salt and a medium chain fatty acid. In some embodiments, the ketogenic composition can include a ketone ester and a medium chain fatty acid.

In some embodiments, the ketogenic composition can include a ketone salt, a ketone body precursor, and a medium chain fatty acid. In some embodiments, the ketogenic composition can include a ketone ester, a ketone body precursor, and a medium chain fatty acid. In some embodiments, the ketogenic composition can include a ketone body precursor and a medium chain fatty acid.

For example, the ketogenic composition can include a sodium/calcium or sodium/potassium βHB mineral salt and a 1,3 butanediol acetoacetate diester. The ketogenic composition can include a sodium/calcium or sodium/potassium βHB mineral salt and a MCT. The composition can include a ketone ester and a medium chain fatty acid. For example, the ketogenic composition can include 1,3 butanediol acetoacetate diester and a MCT. The composition can include a ketone salt and a MCT mixed at an approximate 1:1 ratio. The composition can include a ketone ester and a MCT mixed at an approximate 1:1 ratio. The composition can include a ketone body precursor and a MCT mixed at an approximate 1:1 ratio. In some embodiments, the MCT can include 65% caprylic triglyceride. In some embodiments, the MCT can include 60% caprylic triglyceride and 40% capric triglyceride.

The ketogenic composition can further include other nutritional substrates. For example, the ketogenic composition can further include free amino acids, amino acid metabolites, vitamins, minerals, electrolytes and metabolic optimizers such as NADH, soluble ubiquinol, tetrahydrobiopterin, alpha-ketoglutaric acid, carnitine, and/or alpha lipoic acid, nutritional co-factors, calcium beta-methyl-beta-hydroxybutyrate, arginine alpha-ketoglutarate, sodium R-alpha lipoic acid, thiamine, riboflavin, niacin, pyridoxine, ascorbic acid, citric acid, malic acid, sodium benzoate, potassium sorbate, acesulfame K, aspartame, xanthan gum, or a combination thereof. Non-limiting examples of nutritional co-factors include R-alpha lipoic acid, acetyl-1-carnitine, ketoisocaproate, alpha-ketoglutarate, alpha-hydroxyisocaproate, creatine, branched chain amino acids (leucine, isoleucine, valine), beta-hydroxy-beta methylbutyrate (HMB), B vitamins, vitamin C, soluble ubiquinol, and carnitine that assist in mitochondrial function.

In some embodiments, the ketogenic composition can be in a variety of forms. For example, the ketogenic composition can be in solid form, semi-solid form, or a liquid dosage forms. The ketogenic composition can be in the form of tablets, pills, powders, liquid solutions or suspensions, suppositories, and injectable or infusible solutions. The preferred form depends on the intended mode of administration and therapeutic application.

In some embodiments, the ketogenic composition can be a solid, for example a powder, tablet, gel, bar, confectionary product, or a granule, and intended for use as a solid oral dose form. The solid composition can be mixed before use with a liquid, such as a water-based liquid (e.g., fruit drink, dairy product, milk, and yogurt), to provide a liquid drink for the user. The ketogenic composition can be provided, as desired, as a liquid product in a form ready for consumption or as a concentrate or paste suitable for dilution on use. The liquid product can be pH adjusted with citric and/or malic acid, and artificial sweetener and flavoring can be added. The liquid product can be homogenized and pasteurized. The ketogenic composition can further include a pharmaceutically acceptable excipient, diluent, or carrier.

The ketogenic composition can further include a pharmaceutically acceptable carrier or excipient. Such carriers may be sterile liquids, such as water and oils. For example, the carrier can be a petroleum oil such as mineral oil; vegetable oil such as peanut oil, soybean oil, or sesame oil; animal oil; or oil of synthetic origin. Suitable carriers can also include ethanol, dimethyl sulfoxide, glycerol, silica, alumina, starch, sorbitol, inositol, xylitol, D-xylose, mannitol, powdered cellulose, microcrystalline cellulose, talc, colloidal silicon dioxide, calcium carbonate, magnesium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers. Suitable carriers can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The ketogenic composition can contain minor amounts of wetting or emulsifying agents. The ketogenic composition can contain pH buffering agents.

In some embodiments, the ketogenic composition can be delivered to the subject in any dose sufficient to achieve the desired therapeutic effect. For example, the ketogenic composition can be administered in a dosage range of 1 mg ketogenic compound/kg of body weight to 100 g ketogenic compound/kg body weight. A therapeutically effective amount of a ketogenic compound can be 1 mg ketogenic compound/kg body weight to 25,000 mg/kg, 5 mg/kg to 10,000 mg/kg, 10 mg/kg to 5,000 mg/kg, 15 mg/kg to 1,000 mg/kg, 20 mg/kg to 800 mg/kg, 25 mg/kg to 750 mg/kg, 30 mg/kg to 700 mg/kg, 35 mg/kg to 650 mg/kg, 40 mg/kg to 600 mg/kg, 45 mg/kg to 550 mg/kg, 50 mg/kg to 500 mg/kg, 55 mg/kg to 450 mg/kg, 60 mg/kg to 400 mg/kg, 65 mg/kg to 350 mg/kg, 70 mg/kg to 300 mg/kg, 75 mg/kg to 250 mg/kg, 80 mg/kg to 200 mg/kg, 85 mg/kg to 150 mg/kg, and 90 mg/kg to 100 mg/kg. A therapeutically effective amount of a ketogenic compound can be 1.25 mg/kg, 2.5 mg/kg, 5 mg/kg, 10 mg/kg, 50 mg/kg, 100 mg/kg, 500 mg/kg, 1,000 mg/kg, 1,500 mg/kg, 2,000 mg/kg, 2,500 mg/kg, 3,000 mg/kg, 3,500 mg/kg, 4,000 mg/kg, 4,500 mg/kg, 5,000 mg/kg, 7,500 mg/kg, 10,000 mg/kg, 25,000 mg/kg, 50,000 mg/kg, or 100,000 mg/kg.

The ketogenic composition can be administered in various ways, including, for example, orally, intragastrically, or parenterally (referring to intravenously and intra-arterially and other appropriate parenteral routes), among others. Administration of the ketogenic composition can be as a single dose, or multiple doses over a period of time. The ketogenic composition can be administered to the patient at any frequency necessary to achieve the desired therapeutic effect. For example, the ketogenic composition can be administered once to several times every month, every two weeks, every week, or every day. Administration of the ketogenic composition can be repeated until the desired therapeutic effect has been achieved. For example, the ketogenic composition can be administered once to several times over the course of 1 day, 3 days, 5 days, 1 week, 2 weeks, 3 weeks, 1 month, 2 months, 3 months, 4 months, 5 months, 6 months, 7 months, 8 months, 9 months, 10 months, 11 months, 12 months, or more.

Uridine Source

In the methods described herein, uridine source in combination with ketogenic composition can be administered. The term "source" refers to an agent that increases the concentration of the desired agent (uridine, etc.) in the bloodstream or tissues. In some embodiment, the uridine source can metabolized by a tissue, enzyme, or target cell of the subject to the desired compound. Suitable uridine sources or uridine precursors can include, but is not limited to uridine; salts of uridine like uridine phosphates, uridine 5' monophosphate, uridine 5' diphosphate, uridine 5' triphosphate; cytidine, which is converted into uridine by the human liver, cytidine 5' monophosphate, cytidine 5' diphosphate, cytidine 5' triphosphate, CDP-choline; acyl derivatives of uridine; or any combinations thereof. In some embodiments, the uridine source can be uridine (e.g. those disclosed in U.S. Pat. No. 5,470,838). In some embodiments, the uridine source can be uridine phosphate. In another embodiment, the uridine source can be a uridine 5' monophosphate. In another embodiment, the uridine source can be a uridine 5' diphosphate. In another embodiment, the uridine phosphate can be a uridine 5' triphosphate. In some embodiments, the uridine source can be cytidine. In some embodiments, the uridine source can be a cytidine 5' monophosphate. In some embodiments, the uridine source can be a cytidine 5' diphosphate. In some embodiments, the uridine source can be a cytidine 5' triphosphate. In some embodiments, the uridine source can be a CDP-choline. In some embodiments, the uridine source can be acyl derivatives of uridine.

In some embodiments, uridine source can be in a variety of forms. For example, uridine source can be in solid form, semi-solid form, or a liquid dosage forms. In some embodiments, uridine source can be in the form of tablets, pills, powders, liquid solutions or suspensions, suppositories, and injectable or infusible solutions. The preferred form depends on the intended mode of administration and therapeutic application.

In some embodiments, uridine source can be a solid, for example a powder, tablet, gel, bar, confectionary product, or a granule, and intended for use as a solid oral dose form. The solid can be mixed before use with a liquid, such as a water-based liquid (e.g., fruit drink, dairy product, milk, and yogurt), to provide a liquid drink for the user. Uridine source can be provided, as desired, as a liquid product in a form ready for consumption or as a concentrate or paste suitable for dilution on use. The liquid product can be pH adjusted with citric and/or malic acid, and artificial sweetener and flavoring can be added. The liquid product can be homogenized and pasteurized. Uridine source can further include a pharmaceutically acceptable excipient, diluent, or carrier.

Uridine source can further include a pharmaceutically acceptable carrier or excipient. Such carriers may be sterile liquids, such as water and oils. For example, the carrier can be a petroleum oil such as mineral oil; vegetable oil such as peanut oil, soybean oil, or sesame oil; animal oil; or oil of synthetic origin. Suitable carriers can also include ethanol, dimethyl sulfoxide, glycerol, silica, alumina, starch, sorbitol, inositol, xylitol, D-xylose, mannitol, powdered cellulose, microcrystalline cellulose, talc, colloidal silicon dioxide, calcium carbonate, magnesium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers. Suitable carriers can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Uridine source can contain minor amounts of wetting or emulsifying agents. Uridine source can contain pH buffering agents.

In some embodiments, the uridine source can be delivered to the subject in any dose sufficient to achieve the desired therapeutic effect. For example, the uridine source can be administered in a dosage range of 1 mg uridine/kg of body weight to 100 g uridine/kg body weight. A therapeutically effective amount of uridine source can be 1 mg uridine/kg body weight to 25,000 mg/kg, 5 mg/kg to 10,000 mg/kg, 10 mg/kg to 5,000 mg/kg, 15 mg/kg to 1,000 mg/kg, 20 mg/kg to 800 mg/kg, 25 mg/kg to 750 mg/kg, 30 mg/kg to 700 mg/kg, 35 mg/kg to 650 mg/kg, 40 mg/kg to 600 mg/kg, 45 mg/kg to 550 mg/kg, 50 mg/kg to 500 mg/kg, 55 mg/kg to 450 mg/kg, 60 mg/kg to 400 mg/kg, 65 mg/kg to 350 mg/kg, 70 mg/kg to 300 mg/kg, 75 mg/kg to 250 mg/kg, 80 mg/kg to 200 mg/kg, 85 mg/kg to 150 mg/kg, and 90 mg/kg to 100 mg/kg. A therapeutically effective amount of uridine source can be 1.25 mg/kg, 2.5 mg/kg, 5 mg/kg, 10 mg/kg, 50 mg/kg, 100 mg/kg, 150 mg/kg, 200 mg/kg, 250 mg/kg, 350 mg/kg, 500 mg/kg, 600 mg/kg, 700 mg/kg, 800 mg/kg, 900 mg/kg, or 1000 mg/kg.

Uridine source can be administered in various ways, including, for example, orally, intragastrically, or parenterally (referring to intravenously and intra-arterially and other appropriate parenteral routes), among others. Administration can be as a single dose, or multiple doses over a period of time. Administration can be as a single dose, or multiple doses over a period of time. In an embodiment, uridine source can be administered chronically, for example, between 1 day and 7 days), or sub-chronically (e.g., more than 7 days). For example, multiple doses can be delivered over 1 day, 3 days, 5 days, 7 days, 10 days, 14 days, or more, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or more, 1 month, 2 months, 3 months, 4 months, 5 months, 6 months, 7 months, 8 months, 9 months, 10 months, 11 months, 12 months, or more.

Additional Therapies

In the methods described herein, additional therapies can be administered simultaneously or sequentially with the administration of uridine source in combination with a ketogenic composition. For example, additional therapies for the treatment or prevention of seizures can be administered to the subject. Sequential administration includes administration before or after administration of uridine source in combination with a ketogenic composition. In other embodiments, there may be an interval of time between administration of the additional therapeutic agent and the administration of uridine source in combination with a ketogenic composition. In some embodiments, the additional therapeutic agent or agents can be administered simultaneously with the administration of uridine source in combination with a ketogenic composition. In some embodiments, administration of an additional therapeutic agent with the administration of uridine source in combination with a ketogenic composition can allow lower doses of the other therapeutic agents and/or administration at less frequent intervals. When used in combination with one or more other active ingredients, the uridine source in combination with a ketogenic composition and the other active ingredients can be used in lower doses than when each is used individually.

For example, the uridine source in combination with a ketogenic composition can be administered in combination with antiepileptic agents such as sodium valproate, carbamazepine, lamotrigine, levetiracetam, topiramate; anticonvulsant agents such as phenyloin sodium, diazepam, and the like; antidepressants such as isocarboxazid, amoxapine, and the like, muscle relaxants, and the like. Other therapies may include brain surgery, vagus nerve stimulation, deep brain stimulation, rehabilitation therapies, including physical therapy, occupational therapy, speech therapy, cognitive therapy, and the like.

Kits

Disclosed herein are kits, which may be used to treat seizures in a subject. For example, the kit may be used to prevent or delay seizures in a subject. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

By way of non-limiting illustration, examples of certain embodiments of the present disclosure are given below.

Examples

Both uridine and exogenous ketone supplements decreased the number of spike-wave discharges (SWDs) in a rat model of human absence epilepsy Wistar Albino Glaxo/Rijswijk (WAG/Rij) rats. It has been suggested that alleviating influence of both uridine and ketone supplements on absence epileptic activity may be modulated by $A_1$ type adenosine receptors ($A_1Rs$). The first aim was to determine whether intraperitoneal (i.p.) administration of a specific $A_1R$ antagonist 1,3-dipropyl-8-cyclopentylxanthine (DPCPX; 0.2 mg/kg) and a selective adenosine $A_{2A}$ receptor antagonist (7-(2-phenylethyl)-5-amino-2-(2-furyl)-pyrazolo-[4,3-e]-1,2,4-triazolo[1,5-c]pyrimidine) (SCH 58261; 0.5 mg/kg) have a modulatory influence on i.p. 1000 mg/kg uridine-evoked effects on SWD number in WAG/Rij rats. The second aim was to assess efficacy of a sub-effective dose of uridine (i.p. 250 mg/kg) combined with beta-hydroxybutyrate salt+medium chain triglyceride (KSMCT; 2.5 g/kg, gavage) on absence epilepsy. DPCPX completely abolished the i.p. 1000 mg/kg uridine-evoked alleviating effect on SWD number whereas SCH 58261 was ineffective, confirming the $A_1R$ mechanism. Moreover, the sub-effective dose of uridine markedly enhanced the effect of KSMCT (2.5 g/kg, gavage) on absence epileptic activity. These results demonstrate the anti-epilepsy benefits of co-administrating uridine and exogenous ketone supplements as a means to treat absence epilepsy.

It has been demonstrated that nucleoside levels and metabolic enzymes, transporters, and receptors of nucleosides are unevenly distributed in the central nervous system (CNS) of animals and humans suggesting region-dependent roles of nucleosidergic system in the brain [1]. Indeed, for example, adenosine and uridine have a role in the modulation of physiological and pathophysiological processes in the brain, such as synaptic plasticity, inflammation, and epilepsy [2-4]. It was recently demonstrated that uridine has an anti-convulsant and anti-epileptic effect on different animal models [3,5,6] such as a model of human absence epilepsy Wistar Albino Glaxo/Rijswijk (WAG/Rij) rats [7,8], but our knowledge relating to its mechanism of action is far from complete. However, it was suggested that uridine is a signaling molecule in the CNS [9-11].

Pyrimidine nucleoside uridine can be synthetized mainly by liver and adipose tissues [12]. As de novo synthesis of pyrimidines in the brain is limited [13] brain utilization is mostly plasma uridine to generate and maintain proper uridine levels for different physiological processes [12]. Uridine molecules can be transported from liver cells to the circulatory system, subsequently enter the brain through the blood-brain barrier and transported through nucleoside transporters into brain cells [14]. Uridine may be metabolized to uridine nucleotides such as uridine triphosphate (UTP) in brain cells [15], which is involved in synthesis of RNA and glycogen molecules as well as membrane lipid phosphatidylcholine [12,16]. Alternatively, uridine may catabolize intracellularly to uracil and subsequently to dihydrouracil by uridine phosphorylase and dihydropyrimidine dehydrogenase, respectively [1,12,15]. Moreover, UTP can be released from brain cells and metabolized extracellularly by ectonucleotidase enzyme cascade to uridine, which uridine can be transported again into the brain cells. The uridine-UTP-uridine cycle can provide local generation of adequate uridine and UTP levels for cellular functions [1,14,15]. In relation to the mechanism of action of uridine in the CNS it was demonstrated, among others, that uridine may bind to its own putative receptor, which receptor has not been cloned yet [11]. It was also suggested that uridine can also modulate different neurotransmitter systems, such as the adenosinergic system, likely via interaction with $A_1$ type adenosine receptors ($A_1Rs$) [9,11].

A great deal of evidence from retrospective long-term studies, multicenter studies, meta-analysis, randomized clinical controlled trials and Cochrane reviews suggests that ketogenic diets (KDs) are effective in the treatment of different types of epilepsies in children, adolescents, and adults with, for example, drug-resistant epilepsy, (super-refractory) status epilepticus and febrile infection-related epilepsy syndrome [17-22]. It has been suggested that not only KDs, but also exogenous ketone supplements (EKSs)-evoked hyperketonemia (increased beta-hydroxybutyrate/ βHB and acetoacetate/AcAc) may have therapeutic potential in the treatment of several diseases, such as epilepsy [23-26]. Ketone bodies can potentiate the repolarization of neuronal membrane, inhibit vesicular glutamate transporters and glutamate release, increase activity of ATP-sensitive potassium channels [27-29], enhance the GABAergic and adenosinergic inhibitory effects [27,30,31], and, as a consequence, change electric activities of neurons and brain networks [32], suppressing neuronal (hyper)excitability, and epileptic activity [30,33,34]. Indeed, it was demonstrated that ketosis may have an important role in KD- and EKSs-generated anti-convulsant and anti-epileptic effects [21,25, 35,36].

Ketone bodies can cross the blood brain barrier by monocarboxylic transporters, metabolize to acetyl-CoA in the cells and provide a source of energy for the nervous tissue cells via Krebs cycle [23,27]. It is widely accepted that ketone bodies, such as βHB, can exert their alleviating effects on different CNS diseases, such as epilepsy by, for example, modified signaling processes, decreased inflammatory processes, enhanced overall metabolism, and suppressed oxidative stress [37-39]. It has also been demonstrated that EKSs, such as ketone ester (KE), and ketone salt (KS), and their mix with medium chain triglyceride (MCT) oils (e.g., KSMCT) generate rapid and sustained nutritional ketosis [25,35,40], which effect decreased not only absence epileptic activity [25], but also the lipopolysaccharide (LPS)-evoked increase in absence epileptic activity in WAG/Rij rats [41]. Moreover, it was also suggested that administration of EKSs may be an alternative metabolic therapy to the KD in the treatment of different CNS diseases, such as epilepsy and psychiatric diseases in which $A_1Rs$ can evoke modulatory influence [25,42].

One of the most investigated rodent models of human absence epilepsy is the WAG/Rij rat strain [43]. All WAG/Rij rats show bilaterally synchronous and spontaneously occurring spike-wave discharges (SWDs) on electroencephalographic (EEG) recordings, which SWDs are initiated in the hyperexcitable neurons in the somatosensory cortex (cortical focus) [44]. Uridine may modulate absence epileptic activity, for example, through interactions with adenosine receptors [7,45] resulting decrease in neuronal hyperexcitability, and, as a result, in SWD number in WAG/Rij rats. It was suggested that $A_{2A}$ type adenosine receptors ($A_{2A}Rs$) may evoke an increase in absence epileptic activity [46], whereas $A_1Rs$ may have an alleviating influence on absence epilepsy [4,45]. Exogenous ketone supplements may increase adenosine levels in the CNS and can activate $A_1Rs$ by which EKSs may modulate pathophysiological processes and diseases in the CNS, such as epilepsy [4,25,31]. These results suggest that adenosine receptors (likely $A_1Rs$) could modulate the alleviating effect of not only uridine, but also EKSs on absence epileptic activity. Thus, co-administration of uridine and EKSs may enhance their beneficial effects on absence epileptic activity. However, putative modulatory role of inhibitory $A_1Rs$ or excitatory $A_{2A}Rs$ on uridine-evoked beneficial effects on absence epilepsy, as well as influence of co-administration of uridine with EKSs on absence epileptic activity has not been investigated yet. Consequently, first, we tested whether intraperitoneal (i.p.) administration of a non-proepileptic dose of a specific $A_1R$ antagonist 1,3-dipropyl-8-cyclopentylxanthine (DPCPX) and a non-antiepileptic dose of a selective adenosine $A_{2A}$ receptor antagonist (7-(2-phenylethyl)-5-amino-2-(2-furyl)-pyrazolo-[4,3-e]-1,2,4-triazolo [1,5-c]pyrimidine) (SCH 58261) have modulatory effect on i.p. 1000 mg/kg uridine-evoked alleviating influence on absence epileptic activity in WAG/Rij rats. Moreover, it has been demonstrated previously that KSMCT (2.5 g/kg) gavage-evoked increase in blood βHB level reached the therapeutic level of ketosis (2-7 mmol/L) [24] after one hour of the treatment (~2.3 mmol/L) [47], decreased slightly (≈1.8 mmol/L) about one hour later [25], but did not change significantly the SWD number on the first day of application, compared to control [25]. Theoretically, to increase the effectivity of KSMCT on absence epileptic activity we could increase its dose or use drugs together with KSMCT, which can enhance effect of KSMCT. However, increased dose of EKSs or several drugs may enhance not only their alleviating influences, but also putative adverse effects. Furthermore, administration of compounds—such as uridine—that can enhance the alleviating effects of ketosis could provide relief and flexibility to a broad array of patients struggling with epilepsy (or other disorders), including those on KDs. For example, it would allow the patients to partly liberate their diet and make it more palatable (e.g., reduced % of fat), which may increase efficacy and tolerability and decrease side effects. Consequently, administration of low dose uridine in combination with KDs or exogenous ketone supplements may have strong clinical potential. Thus, to reveal the influence of uridine on KSMCT-generated effect on absence epileptic activity, a smaller and single dose of uridine (i.p. 250 mg/kg) was used in combination with KSMCT (2.5 g/kg, gavage) in the second part of the study. Based on previous studies [4,11,25,41] we hypothesized that adenosine receptor antagonists may modulate the uridine-evoked effect on SWD number and uridine may increase the KSMCT-evoked influence on absence epileptic activity in WAG/Rij rats. The focus of the current study was to test a co-administrated therapeutic strategy and mechanism for suppressing absence epileptic activity that is unlike any anti-epilepsy drug (AED) currently in use.

Materials and Methods

Implantation of Screw Electrodes for Detection of EEG Signals

All parts of experiments were approved similarly to our previous study [25] by the Animal Care and Experimentation Committee of the Savaria University Centre (ELTE, Hungary; license number: VA/ÉBNTF02/85-8/2016). Number of experimental animals for this study was reduced to minimal and pain and suffering were minimized Male WAG/Rij rats (n=52; 10 months old, 335-357 g) were used (breeding colony of WAG/Rij rats at Savaria University Centre, Szombathely, Hungary). Free access to water and food (Table 1), as well as standard laboratory conditions were provided [25].

TABLE 1

Macronutrient ratios of rodent standard diet.

| | |
|---|---|
| % Cal from Fat | 10.0 |
| % Cal from Protein | 23.0 |
| % Cal from Carbohydrates | 67.0 |
| kcal/g | 3.3 |

Rats were implanted with stainless steel screw electrodes for EEG recording under isoflurane-air mixture (2.0-2.5%) anesthesia [25]. The screw electrodes were placed epidurally over the cortex of the frontal (AP: 2.0 mm; L: 2.1 mm) and parietal (AP: −6.5 mm; L: 2.1 mm) areas [48]. Reference electrodes and ground electrodes were also stainless-steel screw electrodes (implanted above the cerebellar cortex) [49]. All electrodes were soldered to a 10-pin socket and permanently attached to the skull with dentacrylate cement (Ivoclar Vivadent AG, Schaan, Liechtenstein). Lidocaine ointment (5%; EGIS, Budapest, Hungary) was used as post-operative pain relief.

The EEG was recorded in a Faraday cage. EEG signals were fed to an electroencephalograph (NIHON-KOHDEN, Tokyo, Japan)-CED (Cambridge Electronic Design Ltd., Cambridge, UK; POWER 1401 mkII) system. The sampling rate was 500 Hz whereas the bandwidth of the EEG recording was 0.3 Hz to 150 Hz. Both the treatments and handling may induce stress and behavioral changes, which may modify the SWD number [7,50,51]. However, it was observed [7,51] that behavioral changes disappeared within 25-30 min after treatments and normal SWD morphology was also demonstrated. For this reason, data of the first 30 min after the treatments was excluded from the analysis. Thus, the number and time of SWDs were considered between 30 and 270 min of post-treatment time (from 1.00 PM to 5.00 PM). SWDs (a train of asymmetric 7-11 Hz sharp spikes and slow waves) were cut off from the raw data files and were analyzed by FFT analysis [51]. The recording periods were split into 60 min sections and evaluated separately.

Treatment Groups

Based on previous results on WAG/Rij rats [8,25,46], the effective and well-tolerated dose of uridine (i.p. 250 mg/kg and 1000 mg/kg; Sigma-Aldrich, Inc., Budapest, Hungary), a non-proepileptic dose of DPCPX (i.p. 0.2 mg/kg; Sigma-Aldrich, Inc., Budapest, Hungary), a non-antiepileptic dose of SCH 58261 (i.p. 0.5 mg/kg; Sigma-Aldrich, Inc., Budapest, Hungary) and KSMCT (2.5 g/kg; mix of KS and MCT in a 1:1 ratio; gavage) were used alone and in combination. KS consisted of $Na^+/K^+$-βHB mineral salt [35] whereas MCT oil contained ≈60% caprylic triglyceride and 40% capric triglyceride (Now Foods, Bloomingdale, IL, USA). It has been demonstrated that 1-30% dimethyl sulfoxide (DMSO) solution did not modify absence epileptic activity in WAG/Rij rats [52]. Thus, 10% DMSO (Sigma-Aldrich Inc., Budapest, Hungary) solution was used to dissolve the DPCPX and SCH 58261, whereas uridine was dissolved in saline [8,25,46].

It has been previously demonstrated that effective doses of uridine, DPCPX, SCH 58261, EKSs (such as KSMCT) did not change sleep-waking ratios and averaged time of SWDs (consequently, changes in total time of SWDs were parallel with alteration of SWD number) or discharge frequency within SWDs [7,8,25,41,45]. Consequently, in this study, we focused on changes in SWD number evoked by uridine (250 mg/kg and 1000 mg/kg) alone (group 1, n=6; and group 2, n=6), DPCPX (0.2 mg/kg) alone (group 3, n=6), SCH 58261 (i.p. 0.5 mg/kg) alone (group 4, n=6) and KSMCT alone (group 7, n=8). However, we had no prior data on putative influence of combined administration of DPCPX with uridine, SCH 58261 with uridine, as well as uridine with KSMCT on SWD time. Thus, we investigated effects of these combinations of drugs and KSMCT (group 5, n=6; group 6, n=6; and group 8, n=8) on not only SWD number, but also averaged SWD time and total SWD time (between 150 and 210 min).

Animals were assigned into eight groups (FIG. 1). To help the rats to adapt to the experimental procedures (e.g., EEG recording), after the two-week recovery period animals were handled daily and were connected to the EEG/CED system for 4 days (once a day, for 4.5 h) (group 1-8). Moreover, on same days, rats of group 7 and group 8 were also gavaged by water (2.5 g/kg/day) for the adaptation of rats to gavage method [25]. To establish averaged control SWD numbers (group 1-8) and control average time and total time of SWDs (group 5, group 6, and group 8), all rats received 1 mL saline i.p. on 3 consecutive days (three control days, first treatment). Thirty min later, animals were injected again with 1 mL saline i.p. (second treatment, group 1-6) or gavaged by 2.5 g/kg water (second treatment, group 7 and 8). After these treatments (similar to fourth and fifth days of experiments), EEG recordings were carried out. On the fourth day of experiments, the rats in group 1 and group 2 were i.p. injected with 1 mL 10% DMSO solution (first treatment) and, 30 min later, with 250 mg/kg, and 1000 mg/kg uridine in 1 mL saline (second treatment), respectively. On the fourth day, animals in group 3 first received 0.2 mg/kg DPCPX alone in 1 mL 10% DMSO solution (first treatment) followed by i.p. 1 mL saline (30 min later; second treatment) (FIG. 1). Animals of group 4 were injected by 0.5 mg/kg SCH 58261 in 1 mL 10% DMSO solution (first treatment) and by i.p. 1 mL saline (30 min later; second treatment) on the fourth day. On that day, the animals in group 5 were injected with combined i.p. injection of DPCPX and uridine: 0.2 mg/kg DPCPX in 1 mL 10% DMSO solution (first treatment) and, 30 min later, 1000 mg/kg uridine in 1 mL saline (second treatment) were administered. In the case of group 6, animals were injected similar to group 5 on the fourth day, but the first injection contained 0.5 mg/kg SCH 58261. Animals of group 1-6 were i.p. injected with two saline injections similar to control days on the fifth day (post-treatment control/PTC day) to detect the putative long-lasting effects of treatments on SWD number. Animals of group 7 received i.p. 1 mL saline (first treatment), and 30 min later, gavage of 2.5 g/kg KSMCT was carried out (second treatment) on the fourth day. In relation to group 8, animals were treated similar to group 7 on fourth days, but the first treatment was i.p. 250 mg/kg uridine in 1 mL saline. On the fifth (PTC) day, i.p. administration of 1 mL saline (first treatment) was followed by gavage of 2.5 g/kg water (30 min later; second treatment; group 7 and 8) (FIG. 1).

Detection of R-βHB and Glucose Levels

To investigate the effect of KSMCT on blood βHB and glucose levels we measured them on the last (third) control day (control), on the days of the KSMCT gavage (fourth day of experiments) and on the PTC day (fifth day of experiments) after EEG measurements (group 7) by the Precision Xtra™ glucose and ketone monitoring system (Abbott Laboratories, Abbott Park, IL, USA). As the device is able to detect only R-βHB level, the measured βHB level would be lower than the total blood ketone body level (R-βHB+

L-βHB+AcAc+acetone). Although the Precision Xtra™ is R-βHB specific, it remains to be determined in a separate, later study whether the use of racemic mixture exogenous ketones is inferior to enantiomerically pure substances (e.g., competition between R and L forms is plausible). Blood, which was used for detection of R-βHB (mmol/L) and glucose (mg/dl) levels, was taken from the tail veins [25,41] (group 7).

Statistical Analysis

Data were presented as means±standard error of the mean (S.E.M.). The pretreatment control values of SWD numbers (group 1-8) and SWD time (group 5, group 6, and group 8) were the grand average of SWD numbers and time recorded on the three control days. In case of blood level of R-βHB and glucose after KSMCT gavage (group 7), the changes were calculated from the values measured on the last (third) control days. Data analysis was performed by GraphPad PRISM version 6.0a. Analysis was performed using two-way analysis of variance (ANOVA) in order to test the significance of the effect of treatment and time after administration. Significance was calculated by Tukey's multiple comparisons test [40]. Results were considered significant when $p<0.05$.

Results

Effect of Uridine, DPCPX, and SCH 58261 Alone on SWD Number

Figure 2A:
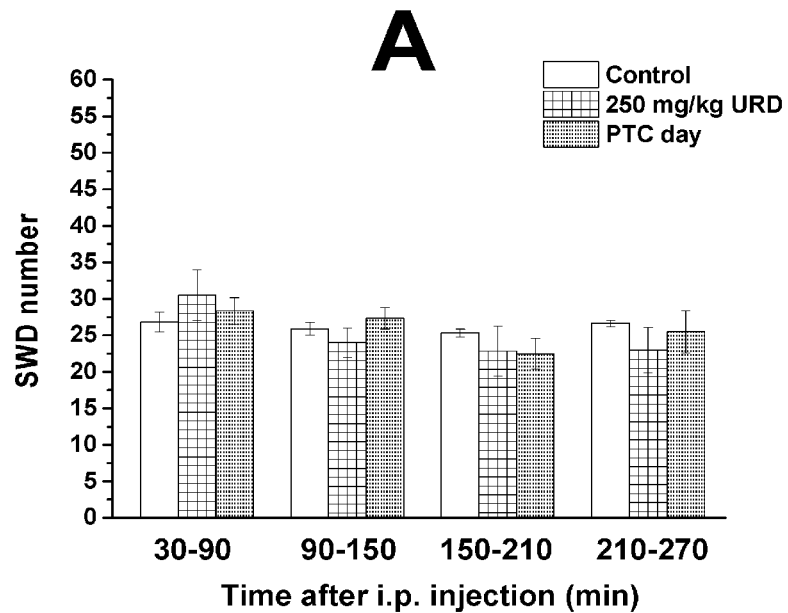
FIGS. 2A-2H show effects of uridine (i.p. 250 mg/kg.
Figure 2B:
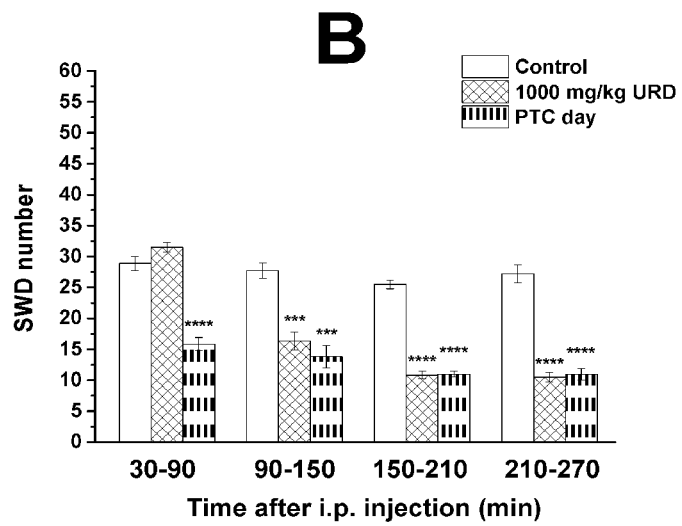

Similar to previous studies [8,46], normal behavior and typical SWDs were detected in all animals 30 min after the connection of rats to the EEG/CED system. After i.p. 250 mg/kg uridine alone, a trend of non-significant decrease in SWD number was observed during second, third and fourth hours of recording periods, compared to control (group 1, FIG. 2A). On the PTC day, significant change in SWD number was not observed (group 1, FIG. 2A). We confirmed our previous result [7,8], that i.p. 1000 mg/kg uridine alone significantly decreased the SWD number between 90 and 270 min, compared to control (between 90 and 150 min, $p=0.0004$; 150 and 210 min as well as 210 and 270 min, $p<0.0001$) (group 2, FIG. 2B). Moreover, significantly decreased SWD number was observed not only on the day of i.p. uridine (1000 mg/kg) injection, but also one day after the uridine administration (PTC day), between 30 and 270 min, compared to control (between 30 and 90 min, 150 and 210 min, as well as 210 and 270 min, $p<0.0001$; 90 and 150 min, $p=0.0004$) (group 2, FIG. 2B).

Figure 2C:
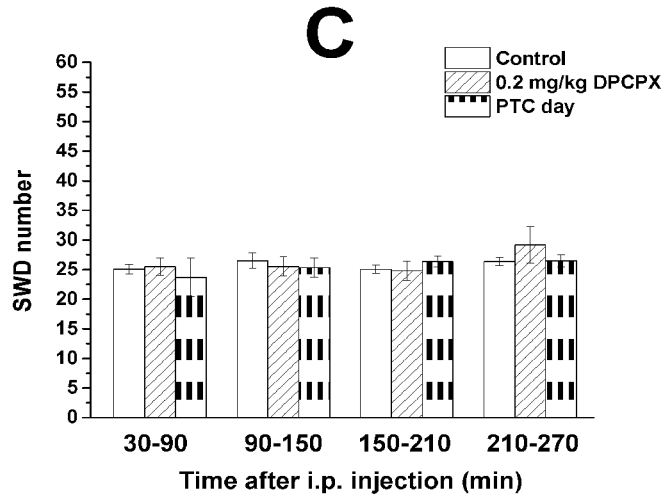
Figure 2D:
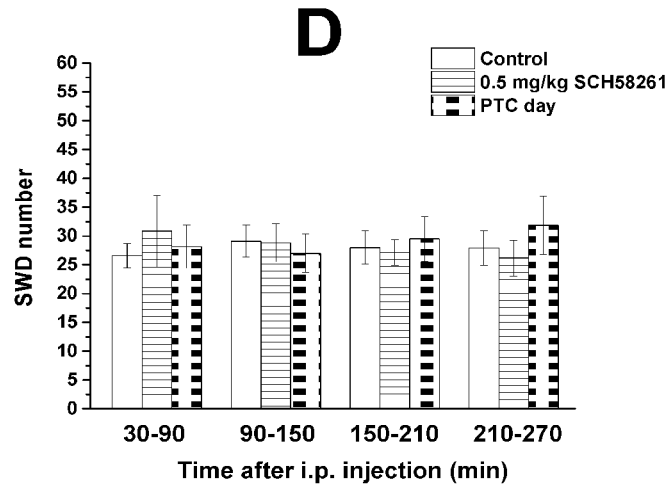

We also confirmed previous result in WAG/Rij rats that i.p. 0.2 mg/kg DPCPX did not evoke proepileptic effect in WAG/Rij rats, not only between 30 and 150 min after i.p. injection of DPCPX (as it was demonstrated previously) [25], but also between 150 and 270 min of recording periods, compared to control (group 3, FIG. 2C). Administration of SCH 58261 (i.p. 0.5 mg/kg) did not generate anti-epileptic effect during the four hours recording period (group 4, FIG. 2D) and, similarly to DPCPX, it did not change SWD number on PTC days, compared to control (group 3 and group 4, FIG. 2C,D).

Figure 2E:
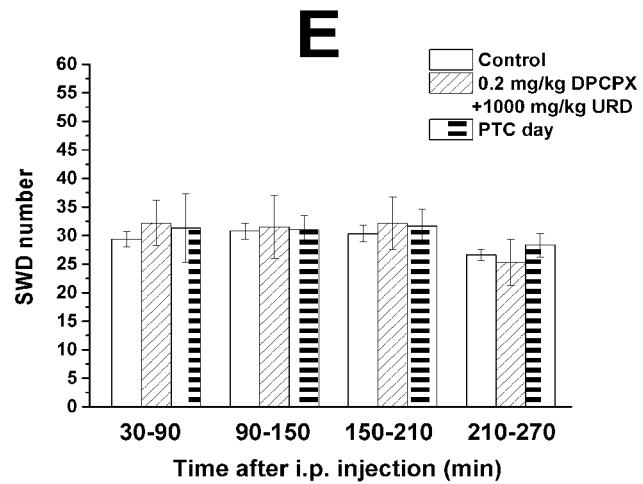
Figure 2F:
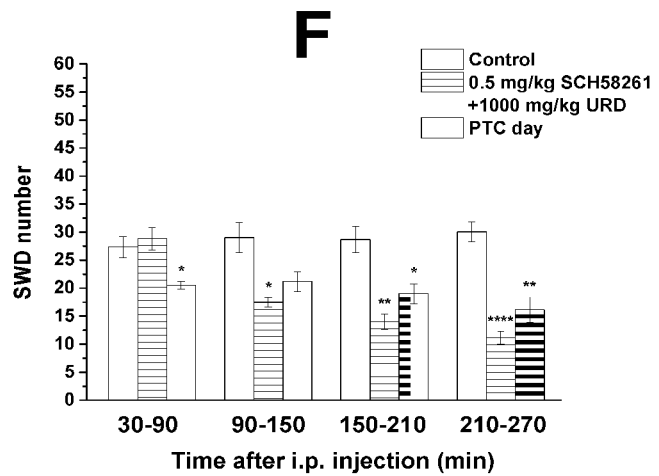

Effect of Combined Administration of DPCPX and SCH 58261 on Uridine-Evoked Decrease in SWD Number and SWD Time Combined administration of i.p. DPCPX (0.2 mg/kg) with i.p. uridine (1000 mg/kg) abrogated the anti-epileptic (SWD number decreasing) effect of uridine (1000 mg/kg) alone (group 5; FIG. 2E) (between 30 and 90 min, $p=0.7946$; 90 and 150 min, $p=0.9909$; 150 and 210 min, $p=0.9240$; 210 and 270 min, $p=0.9514$). In addition, i.p. injection of 0.2 mg/kg DPCPX also abolished the uridine (i.p. 1000 mg/kg) injection-evoked decrease in SWD number on PTC day (group 5; FIG. 2E) (between 30 and 90 min, $p=0.9481$; 90 and 150 min, $p=0.9964$; 150 and 210 min, $p=0.9153$; 210 and 270 min, $p=0.7398$). Nevertheless, i.p. administration of SCH 58261 (0.5 mg/kg) mitigated, but did not abolish the alleviating effect of i.p. uridine (1000 mg/kg) on SWD number on days of both uridine injection days (between 90 and 150 min, $p=0.0152$; 150 and 210 min, $p=0.0014$; 210 and 270 min, $p<0.0001$) and on PTC days (between 30 and 90 min, $p<0.0311$; 90 and 150 min, $p=0.0873$; 150 and 210 min, $p=0.0206$; 210 and 270 min, $p=0.0019$), compared to control (group 6; FIG. 2F).

Figure 2G:
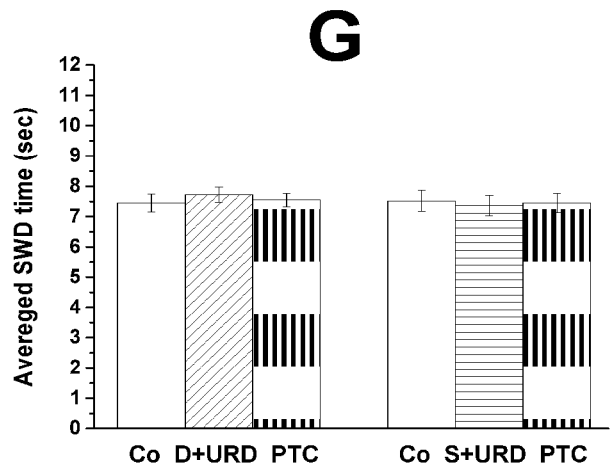
Figure 2H:
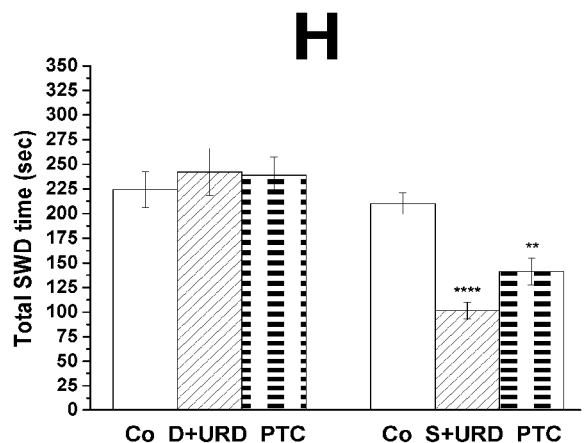

Injection of both DPCPX and SCH 58261 in combination with uridine did not change averaged time of SWDs (group 5, DPCPX+uridine: control vs. treatment day, $p<0.7524$ and control vs. PTC day, $p<0.9601$; group 6, SCH 58261+uridine: control vs. treatment day, $p<0.9471$ and control vs. PTC day, $p<0.9893$) (FIG. 2G). Consequently, alterations of total time of SWDs were parallel with the change in SWD number (group 5, DPCPX+uridine: control vs. treatment day, $p<0.8129$ and control vs. PTC day, $p<0.8716$; group 6, SCH 58261+uridine: control vs. treatment day, $p<0.0001$ and control vs. PTC day, $p<0.0014$) (FIG. 2H).

KSMCT-Evoked Changes in Blood R-βHB and Glucose Levels and SWD Number

Figure 3A:
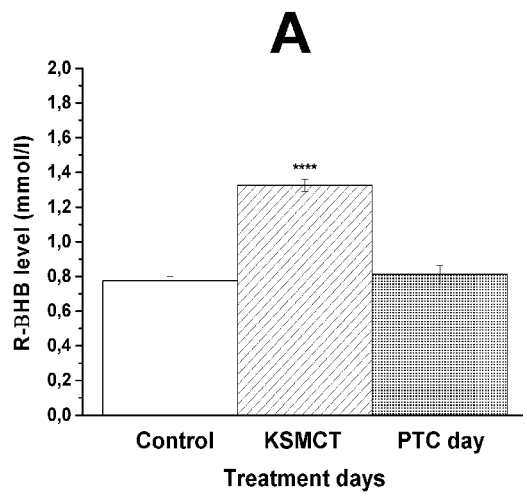
FIGS. 3A-3F show effects of KSMCT (2.5 g/kg, gavage) alone on blood R-βHB (FIG. 3A) and glucose levels (FIG. 3B) as well as SWD number (FIG. 3C). Influence of combined administration of uridine (i.p. 250 mg/kg) with KSMCT (2.5 g/kg, gavage) on SWD number (FIG. 3D) between 30 and 270 min and averaged SWD time (FIG. 3E) and total SWD time (FIG. 3F) between 150 and 210 min Abbreviations: i.p., intraperitoneal; KSMCT, mix of ketone salt (KS) and medium chain triglyceride (MCT) oil in a 1:1 ratio; PTC day, post-treatment control day; R-βHB, R-beta-hydroxybutyrate; SWD, spike-wave discharge; URD, uridine. : $p<0.01$, *: $p<0.001$, ****: $p<0.0001$.
Figure 3B:
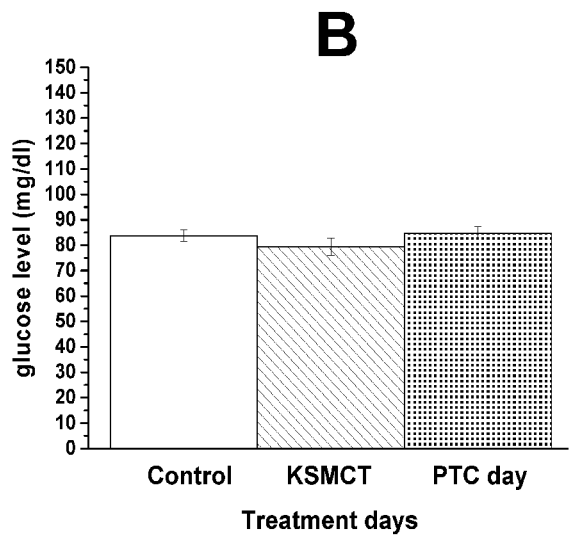

Gavage of 2.5 g/kg KSMCT significantly increased the blood level of R-βHB on the day of administration (group 7; FIG. 3A; $p<0.0001$) whereas after one day of gavage (on PTC day), R-βHB level returned to the control level (group 7; FIG. 3A; $p=0.78$), compared to control. KSMCT gavage did not change blood level of glucose (group 7; FIG. 3B).

Figure 3C:
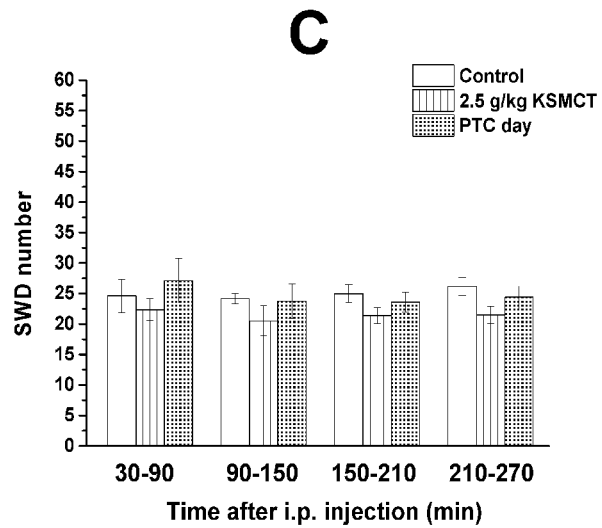

We confirmed that single administration of 2.5 g/kg KSMCT (gavage) did not change significantly the SWD number in WAG/Rij rats, not only between 30 and 150 min after gavage [25] but also between 150 and 270 min of recording period, compared to control (group 7, FIG. 3C). However, a trend of a non-significant decrease in SWD number was observed during four hours of recording periods, compared to control (group 7, FIG. 3C). Moreover, SWD number returned to the control level on the PTC days (group 7, FIG. 3C).

Effect of Combined Administration of Uridine and KSMCT on SWD Number and SWD Time Co-administration of previously established sub-effective dose of uridine (i.p. 250 mg/kg) and KSMCT (2.5 g/kg, gavage) significantly decreased the SWD number during second ($p=0.002$), third ($p=0.0001$), and fourth ($p<0.0001$) hours of recording periods, compared to control (group 8, FIG. 3D), suggesting a synergistic effect. Moreover, SWD number decreased between 90 and 270 min of recording period on PTC days, compared to control, but these changes were not significant (between 90 and 150 min, $p=0.4969$; 150 and 210 min, $p=0.0592$; 210 and 270 min, $p=0.1374$).

Figure 3D:
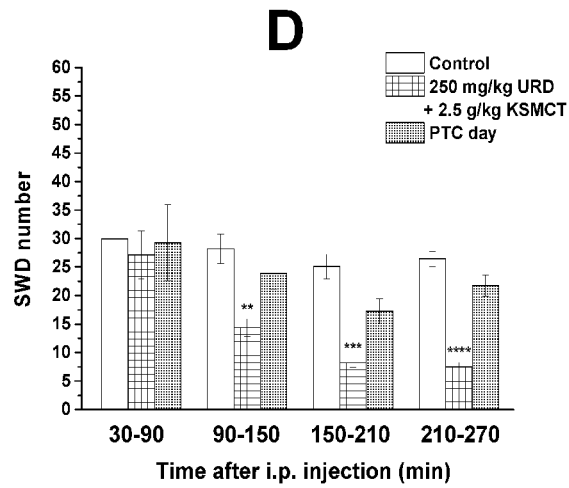
Figure 3E:
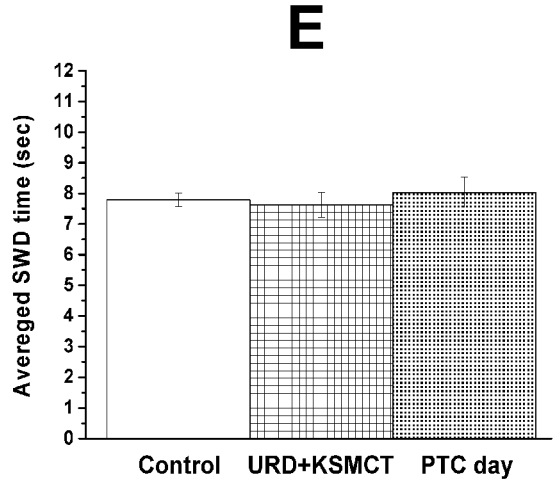
Figure 3F:
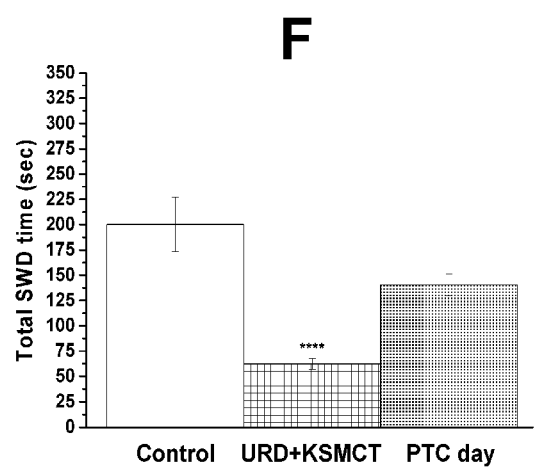

Combined administration of i.p. 250 mg/kg uridine with 2.5 g/kg KSMCT (group 8) did not change average time of SWDs on the treatment days and PTC days (control vs. treatment day, $p=0.9601$ and control vs. PTC day, $p=0.9033$) (FIG. 3E); thus, changes in total time of SWDs were parallel with the alteration of SWD number (control vs. treatment day, $p<0.0001$ and control vs. PTC day, $p<0.0535$) (FIG. 3F).

Discussion

We confirmed previous results that i.p. 1000 mg/kg uridine decreased the SWD number between 90 and 270 min of recording period [7,8] (FIG. 2B), i.p. 0.2 mg/kg DPCPX did not generate changes in SWD number [25] (FIG. 2C) and single administration of 2.5 g/kg KSMCT (gavage) was not able to significantly decrease the SWD number [25] (FIG.

3C) in WAG/Rij rats. The present study demonstrated that the $A_1R$ antagonist DPCPX (i.p. 0.2 mg/kg) abolished the uridine-generated alleviating effects on SWD number, not only on the day of uridine injection (i.p. 1000 mg/kg), but also one day after the injection (PTC day) (FIG. 2E). Moreover, a lower (previously established sub-effective) dose of uridine (i.p. 250 mg/kg) alone evoked only a trend of non-significant decrease in SWD number (FIG. 2A), but administration of this dose of uridine with KSMCT (2.5 g/kg, gavage) significantly decreased the SWD number (FIG. 3D). Finally, previous results on the effect of both DPCPX and KSMCT on SWD number were extended: i.p. 0.2 mg/kg DPCPX had no proepileptic effects, not only between 30 and 150 min [25], but also during the third and fourth hours of recording period (FIG. 2C) and after KSMCT (2.5 g/kg) gavage the trend of non-significant decrease in SWD number was detected longer (between 30-270 min) (FIG. 3C) than it was demonstrated previously (30-150 min) [25].

It has been demonstrated that uridine evoked anti-epileptic and anti-epileptogenic effects in different models [3,6], in children with epileptic encephalopathy [53] and in WAG/Rij rats [7,8]. As the uridine is an endogenous molecule, administration of proper doses of uridine in the treatment of epilepsy may be a safe way to evoke anti-epileptic effects without or minimal side effects and considerable risks, compared to pharmacological treatments. Indeed, it has been demonstrated that uridine is a well-tolerated drug with only minor toxic potential, suggesting that uridine and its analogues may be effective and safe anti-epileptic drugs in the treatment of different types of epilepsies [3,4,53,54].

It was suggested that increased level of ketone bodies (e.g., βHB; ketosis) may have therapeutic potential in the treatment of different type of seizures and epilepsies [25, 35,55]; thus, EKSs-evoked ketosis [25,47] (FIG. 3A) may have therapeutic potential in the treatment of absence epilepsy. Indeed, sub-chronically administered EKSs can increase βHB levels and may decrease SWD number in WAG/Rij rats by time-, dose-, and administration-dependent manner [25,41]. Similar to uridine, it was demonstrated that EKSs, such as KEs, proper doses of KSs and MCTs as well as their combinations (e.g., KEKS, KSMCT, and KEMCT) are well-tolerated, safe and efficient ketogenic agents with little or no side effects [25,35,40,56].

In relation to the putative mechanism of action, for example, it has been demonstrated that ketone bodies may increase the level of adenosine and GABA in the brain, which are endogenous anti-convulsants (modulator and transmitter) that can decrease epileptic activity via their inhibitory receptors $A_1Rs$ and $GABA_A$ receptors, respectively [25,31,57,58]. Uridine may also exert its effect via partly the same anti-convulsant (adenosinergic and GABAergic) systems via interactions with Ado receptors and/or $GABA_A$ receptor and putative uridine receptor [11] or by uridine-evoked increase in GABA levels [59]. Moreover, it has been demonstrated that the adenosine released via nucleoside transporters preferentially bind to $A_1Rs$ [60] and uridine was active in eliciting purine (adenosine) release by means of nucleoside transporters [61]. It has also been demonstrated that GABAergic and adenosinergic systems can regulate absence epileptic activity in WAG/Rij rats [8,45]. However, excitatory $A_{2A}Rs$ and $GABA_A$ receptors aggravated the absence epileptic activity [8,45,46] whereas $A_1Rs$ can modulate (decrease) SWD number in WAG/Rij rats [25,41]. Thus, these results suggest that neither $GABA_A$ receptors nor $A_{2A}Rs$ have a role in the alleviating effect of both uridine and EKSs on absence epileptic activity, but $A_1Rs$ can modulate their beneficial, modulatory effects on absence epilepsy. These suggestions were strengthened by this study as i.p. administration of DPCPX abrogated beneficial effect of uridine on SWD number (FIG. 2E) whereas injection of SCH 58261 did not abolish alleviating effect of uridine on absence epileptic activity (e.g., on SWD number) (FIG. 2F). Moreover, co-administration of i.p. uridine and KSMCT (gavage) enhanced the beneficial effect of each other on SWD number, which synergistic effect generated significant decrease in SWD number (e.g., the uridine via interaction between $A_1Rs$ and putative uridine receptors whereas KSMCT via βHB-induced increase in adenosine level and $A_1R$ activation) (FIG. 3D). Thus, these results above suggest that effect of both uridine and KSMCT on absence epileptic activity may be modulated (at least partly) by $A_1Rs$. According to this, it was demonstrated that $A_1Rs$ can inhibit epileptic activity [1,4,45,58,62], brain areas, such as somatosensory cortex, which may have a role in absence epilepsy genesis contain $A_1Rs$ [1,44,45,63] and activity (expression) of $A_1Rs$ was decreased in the somatosensory cortex (cortical focus) in presymptomatic WAG/Rij rats [1,4,45]. By synaptic inhibition, $A_1Rs$, among others, may reduce $Ca^{2+}$ influx and inhibits excitatory synaptic transmission (e.g., decreases the release of glutamate) as well as increase the activity of ATP-sensitive potassium channels [4,60,64]. These effects can hyperpolarize neuronal membranes, decrease neuronal activity and, as a consequence, may decrease absence epileptic activity.

It is possible that uridine may evoke long-term effect on SWD number by modulation of synaptic plasticity [7,10,11, 59,65,66] but our knowledge is not sufficient at present to explain the exact mechanism(s), by which uridine evokes long-lasting effects on SWD number (on PTC days) (FIG. 2B) and by which DPCPX abolished this effect of uridine (FIG. 2E). However, all of the results above suggest that long-term co-administration of uridine with KSMCT may enhance their anti-epileptic influence day by day, which treatment would be more effective in the treatment of absence epilepsy than their single administration. However, studies can be performed to demonstrate the putative alleviating effect of chronic co-administration of uridine and KSMCT on absence epileptic activity not only in animals, but also in humans.

The results suggest that co-administration of a sub-effective dose of uridine with KSMCT in WAG/Rij rats evokes a significant and synergistic effect on suppressing SWD number, which is mediated, in part, by $A_1R$ signaling. The co-administration strategy of uridine and/or EKSs with different anti-epileptics can promote development of more effective treatments in different types of epilepsies, such childhood absence epilepsy and especially therapy-resistant epilepsies. Further animal and clinical studies can be conducted to reveal the exact mechanism(s) of action of uridine-, EKSs-, and adenosine-evoked effects (administered alone or in combination) on epileptic activity, and how this may further augment the efficacy of AEDs or other standard of care therapies.

REFERENCES

1. Kovács, Z., et al., Curr. Top. Med. Chem. 2011, 11, 1012-1033.
2. Haskó, G., et al., Trends Pharmacol. Sci. 2005, 26, 511-516.
3. Zhao, Q., et al., Epilepsy Behav. 2008, 13, 47-51.
4. Kovács, Z., et al., Curr. Med. Chem. 2014, 21, 788-821.
5. Roberts, C. A. Brain Res. 1973, 55, 291-308.

6. Zhao, Q., et al., *Epilepsy Res.* 2006, 70, 73-82.
7. Kovács, Z., et al., *Brain Res. Bull.* 2013, 97, 16-23.
8. Kovács, Z., *Neuroscience* 2015, 300, 593-608.
9. Dobolyi, A., et al., *Curr. Top. Med. Chem.* 2011, 11, 1058-1067.
10. Kardos, J., et al., *Neuroreport* 1999, 10, 1577-1582.
11. Kimura, T., et al., *Sleep* 2001, 24, 251-260.
12. Zhang, Y., et al., *Biomed. Res. Int.* 2020, 2020:7091718.
13. Bourget, P. A., et al., *J. Neurochem.* 1972, 19, 1617-1624.
14. Kovács, Z., et al., *Curr. Med. Chem.* 2013, 20, 4217-4240.
15. Ipata, P. L., et al., *Curr. Top. Med. Chem.* 2011, 11, 909-922.
16. Pooler, A. M., et al., *Neuroscience* 2005, 134, 207-214.
17. deCampo, D. M., et al., *Curr. Opin. Clin. Nutr. Metab. Care.* 2019, 22, 264-268.
18. Freeman, J. M., et al., *Pediatrics.* 1998, 102, 1358-1363.
19. Martin-McGill, K. J., et al., *Cochrane Database Syst. Rev.* 2020, 6, CD001903.
20. Vining, E. P., et al., *Arch. Neurol.* 1998, 55, 1433-1437.
21. Ułamek-Kozioł, M., et al., *Nutrients* 2019, 11, 2510.
22. Ye, F., et al., *J. Clin. Neurol.* 2015, 11, 26-31.
23. Veech, R. L. *Prostaglandins Leukot. Essent. Fatty Acids* 2004, 70, 309-319.
24. Hashim, S. A., et al., *J. Lipid Res.* 2014, 55, 1818-1826.
25. Kovács, Z., et al., *Front. Mol. Neurosci.* 2017, 10, 235.
26. Poff, A. M., et al., *Front. Neurosci.* 2019, 13, 1041.
27. Achanta, L. B., et al., *Neurochem. Res.* 2017, 42, 35-49.
28. Juge, N., et al., *Neuron* 2010, 68, 99-112.
29. Lund, T. M., et al., *J. Neurochem.* 2015, 132, 520-531.
30. McNally, M. A., et al., *J. Neurochem.* 2012, 121, 28-35.
31. Sharma, A. K., et al., *J. Epilepsy Res.* 2015, 5, 1-8.
32. Sada, N., et al., *Front. Cell Neurosci.* 2018, 12, 208.
33. Haas, H. L., et al., *Pflugers Arch.* 1984, 402, 244-247.
34. Simeone, T. A., et al., *Neurochem. Res.* 2017, 42, 2011-2018.
35. D'Agostino, D., et al., *Am. J. Phys. Reg. Integr. Comp. Phys.* 2013, 304, 829-836.
36. Simeone, T. A., et al., *Neuropharmacology* 2018, 133, 233-241.
37. Masino, S. A., et al., *Curr. Neuropharmacol.* 2009, 7, 257-268.
38. Newman, J. C., et al., *Trends Endocrinol. Metab.* 2014, 25, 42-52.
39. Rogawski, M. A., et al., *Cold Spring Harb. Perspect. Med.* 2016, 6, a022780.
40. Ari, C., et al., *Front. Mol. Neurosci.* 2016, 9, 137.
41. Kovács, Z., et al., *Front. Mol. Neurosci.* 2019, 12, 45.
42. Kovács, Z., et al., *Front. Psychiatry* 2019, 10, 363.
43. Coenen, A. M., et al., *Behav. Genet.* 2003, 33, 635-655.
44. Meeren, H. K., et al., *J. Neurosci.* 2002, 22, 1480-1495.
45. D'Alimonte, I., et al., *Eur. J. Neurosci.* 2009, 30, 1023-1035.
46. Lakatos, R. K., et al., *Brain Res. Bull.* 2016, 124, 172-181.
47. Ari, C., et al., *Nutrients* 2019, 11, 2330.
48. Paxinos, G.; Watson, C. The Rat Brain Stereotaxic Coordinates; Academic Press: Orlando, FL, USA, 1998; ISBN-13: 978-0125476171.
49. Sitnikova, E., *Epilepsy Res.* 2009, 84, 159-171.
50. Depaulis, A.; Van Luijtelaar, G. Genetic models of absence epilepsy in the rat. In *Models of Seizures and Epilepsy,* 1st ed.; Pitkänen, A., Schwartzkroin, P. A., Moshé, S. L., Eds; Academic Press, San Diego, CA, USA, 2005; Chapter 18, pp. 233-248.
51. Kovács, Z., et al., *Neuroscience* 2006, 140, 731-742.
52. Kovács, Z., et al., *J. Neurosci. Methods* 2011, 197, 133-136.
53. Koch, J., et al., *Brain* 2017, 140, 279-286.
54. Kimura, T., et al., *Biol. Pharm. Bull.* 2001, 24, 729-731.
55. Ciarlone, S. L., et al., *Neurobiol. Dis.* 2016, 96, 38-46.
56. Clarke, K., et al., *Regul. Toxicol. Pharmacol.* 2012, 63, 401-408.
57. Yudkoff, M., et al., *Annu. Rev. Nutr.* 2007, 27, 415-430.
58. Masino, S. A., et al., *J. Clin. Investig.* 2011, 121, 2679-2683.
59. Liu, P., et al., *Pharmacol. Biochem. Behav.* 2017, 163, 74-82.
60. Cunha, R. A. Purinergic *Signal.* 2005, 1, 111-134.
61. Sperlágh, B., et al., *Br. J. Pharmacol.* 2003, 139, 623-633.
62. Ruskin, D. N., et al., *J. Caffeine Adenosine Res.* 2020, 10, 104-109.
63. Cremer, C. M., et al., *Neuroscience* 2009, 163, 490-499.
64. Lusardi, T. A., et al., *Neuropharmacology* 2015, 99, 500-509.
65. Sakamoto, T., et al., *Brain Res.* 2007, 1182, 50-59.
66. Schäfers, M., et al., *Neurosci. Lett.* 2008, 437, 188-193.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

What is claimed is:

1. A method of treating seizures in a subject, comprising administering to the subject in need thereof an effective amount of a uridine source of from 55 mg/kg to 450 mg/kg and an effective amount of a ketogenic composition comprising a ketone salt and a medium chain triglyceride.

2. The method of claim 1, wherein the ketogenic composition further comprises a ketone ester, a ketone body precursor, or a combination thereof.

3. The method of claim 1, wherein the ketone salt is a β-hydroxybutyrate salt.

4. The method of claim 1, wherein the ketone salt is a β-hydroxybutyrate mineral salt.

5. The method of claim 1, wherein the β-hydroxybutyrate mineral salt is a $Na^+Ca^{2+}$ β-hydroxybutyrate mineral salt.

6. The method of claim 2, wherein the ketogenic composition comprises a ketone ester.

7. The method of claim 6, wherein the ketone ester is 1,3-butanediol-acetoacetate diester.

8. The method of claim 1, wherein the ketone salt and the medium chain triglyceride have an approximate 1:1 ratio.

9. The method of claim 1, further comprising administering an anti-epileptic agent, an anti-convulsant agent, or a combination thereof.

10. The method of claim 1, wherein the method prevents seizures in the subject.

11. The method of claim 1, wherein the method delays the onset of seizures in the in the subject.

12. The method of claim 1, wherein the method reduces the severity of seizures in the subject.

13. The method of claim 1, wherein the subject is diagnosed with a seizure disorder.

14. The method of claim 12, wherein the seizure disorder is epilepsy.

15. The method of claim 1, wherein the composition is administered orally, intraperitoneally, or a combination thereof.

16. The method of claim 1, wherein the subject is a human.

17. A method of suppressing spike wave discharges in a subject, comprising administering to the subject in need thereof an effective amount of a uridine source of from 55 mg/kg to 450 mg/kg and an effective amount of a ketogenic composition comprising a ketone salt and a medium chain triglyceride.

18. The method of claim 17, wherein the method comprises administering to the subject in need thereof an effective amount of a uridine source of 250 mg/kg and an effective amount of a ketogenic composition comprising a ketone salt and a medium chain triglyceride.

19. The method of claim 17, wherein the method comprises administering to the subject in need thereof an effective amount of a uridine source of 250 mg/kg and an effective amount of a ketogenic composition comprising a ketone salt and a medium chain triglyceride.

* * * * *